United States Patent
Elder et al.

(10) Patent No.: US 9,982,282 B2
(45) Date of Patent: May 29, 2018

(54) PROCESS FOR PREPARATION OF SUGARS AND SYRUPS

(71) Applicant: Novozymes A/S, Bagsvaerd (DK)

(72) Inventors: Michael Elder, Wake Forest, NC (US); Randall Deinhammer, Wake Forest, NC (US); Xiaoyuan Cui, Raleigh, NC (US)

(73) Assignee: Novozymes A/S, Bagsvaerd (DK)

( * ) Notice: Subject to any disclaimer, the term of this patent is extended or adjusted under 35 U.S.C. 154(b) by 0 days. days.

(21) Appl. No.: 14/782,642

(22) PCT Filed: Apr. 10, 2014

(86) PCT No.: PCT/US2014/033660
§ 371 (c)(1),
(2) Date: Oct. 6, 2015

(87) PCT Pub. No.: WO2014/169129
PCT Pub. Date: Oct. 16, 2014

(65) Prior Publication Data
US 2016/0168606 A1    Jun. 16, 2016

Related U.S. Application Data

(60) Provisional application No. 61/810,399, filed on Apr. 10, 2013.

(51) Int. Cl.
| | |
|---|---|
| *C12P 19/02* | (2006.01) |
| *C12P 19/20* | (2006.01) |
| *C12P 19/16* | (2006.01) |
| *C12P 19/14* | (2006.01) |
| *C12P 19/24* | (2006.01) |
| *C13K 1/06* | (2006.01) |
| *C13K 11/00* | (2006.01) |

(52) U.S. Cl.
CPC ............ *C12P 19/02* (2013.01); *C12P 19/14* (2013.01); *C12P 19/16* (2013.01); *C12P 19/20* (2013.01); *C12P 19/24* (2013.01); *C13K 1/06* (2013.01); *C13K 11/00* (2013.01); *C12P 2201/00* (2013.01)

(58) Field of Classification Search
None
See application file for complete search history.

(56) References Cited

U.S. PATENT DOCUMENTS

| | | | |
|---|---|---|---|
| 8,617,837 B2 * | 12/2013 | Svendsen | C12N 9/2417 435/202 |
| 2012/0171731 A1 | 7/2012 | Nedwin | |
| 2012/0208251 A1* | 8/2012 | Svendsen | C12N 9/2417 435/162 |

FOREIGN PATENT DOCUMENTS

| | | | |
|---|---|---|---|
| WO | WO1997041213 | * | 11/1997 |
| WO | 2010115021 A2 | | 10/2010 |
| WO | 2013048700 A1 | | 4/2013 |
| WO | 2013057141 A2 | | 4/2013 |
| WO | 2013057143 A1 | | 4/2013 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Liu et al, 2009—NCBI Access No. ACN88150.
Ramachandran et al, 2010, J Microbiol Biotechnol, vol. 20, No. 12, pp. 1696-1701.

* cited by examiner

*Primary Examiner* — Christian Fronda
(74) *Attorney, Agent, or Firm* — Kelly Reynolds

(57) ABSTRACT

The present invention relates to a process for producing a syrup comprising liquefying an aqueous granular starch slurry with an alpha-amylase variant comprising an alteration at one or more positions corresponding to any of positions 1, 2, 68, 71, 126, 133, 142, 144, 156, 158, 176, 185, 201, 205, 213, 239, 279, 316, 318, 360, 416, 437 and 450 of SEQ ID NO: 1 to provide liquefied starch-containing material; saccharifying the liquefied starch-containing material in the presence of a glucoamylase, and a pullulanase derived from *Bacillus deramificans*, *Bacillus subtilis*, *Bacillus amyloderamicans*, or *Bacillus acidopullulyticus* to provide a dextrose syrup, and optionally isomerizing to provide a fructose syrup.

13 Claims, 4 Drawing Sheets

```
                          1                                                50
SEQ ID NO: 1    (1)  ---ANLNGTLMQYFEWYMPNDGQHWRRLQNDSAYLAEHGITAVWIPPAYK
SEQ ID NO: 2    (1)  --AAPFNGTMMQYFEWYLPDDGTLWTKVANEANNLSSLGITALWLPPAYK
SEQ ID NO: 3    (1)  ANTAPINETMMQYFEWDLPNDGTLWTKVKNEAANLSSLGITALWLPPAYK
SEQ ID NO: 4    (1)  ---VPVNGTMMQYFEWYLPDDGTLWTKVANNAQSLANLGITALWLPPAYK
SEQ ID NO: 5    (1)  -GSVPVNGTMMQYFEWYLPDDGTLWTKVANNAQSLANLGITALWLPPAYK
SEQ ID NO: 6    (1)  -----VNGTLMQYFEWYTPNDGQHWKRLQNDAEHLSDIGITAVWIPPAYK
SEQ ID NO: 7    (1)  -HHNGTNGTMMQYFEWYLPNDGNHWNRLRDDAANLKSKGITAVWIPPAWK
SEQ ID NO: 8    (1)  -HHNGTNGTMMQYFEWHLPNDGNHWNRLRDDASNLRNRGITAIWIPPAWK
SEQ ID NO: 9    (1)  -HHNGTNGTMMQYFEWYLPNDGNHWNRLRSDASNLKDKGISAVWIPPAWK
SEQ ID NO: 10   (1)  -HHNGTNGTMMQYFEWYLPNDGNHWNRLRSDASNLKDKGITAVWIPPAWK
SEQ ID NO: 11   (1)  -HHNGTNGTMMQYYEWYLPNDGNHWNRLNSDASNLKSKGITAVWIPPAWK
SEQ ID NO: 12   (1)  ---DGLNGTMMQYYEWHLENDGQHWNRLHDDAAALSDAGITAIWIPPAYK
SEQ ID NO: 13   (1)  ---ANLNGTLMQYFEWYMPNDGQHWKRLQNDSAYLAEHGITAVWIPPAYK
SEQ ID NO: 14   (1)  -----VNGTLMQYFEWYTPNDGQHWKRLQNDAEHLSDIGITAVWIPPAYK 51                                               100
SEQ ID NO: 1   (48)  GTSQADVGYGAYDLYDLGEFHQKGTVRTKYGTKGELQSAIKSLHSRDINV
SEQ ID NO: 2   (49)  GTSRSDVGYGVYDLYDLGEFNQKGTVRTKYGTKAQYLQAIQAAHAAGMQV
SEQ ID NO: 3   (51)  GTSQSDVGYGVYDLYDLGEFNQKGTIRTKYGTKTQYIQAIQAAKAAGMQV
SEQ ID NO: 4   (48)  GTSSSDVGYGVYDLYDLGEFNQKGTVRTKYGTKTQYIQAIQAAHTAGMQV
SEQ ID NO: 5   (50)  GTSSSDVGYGVYDLYDLGEFNQKGTVRTKYGTKTQYIQAIQAAHTAGMQV
SEQ ID NO: 6   (46)  GLSQSDNGYGPYDLYDLGEFQQKGTVRTKYGTKSELQDAIGSLHSRNVQV
SEQ ID NO: 7   (50)  GTSQNDVGYGAYDLYDLGEFNQKGTVRTKYGTRNQLQAAVTSLKNNGIQV
SEQ ID NO: 8   (50)  GTSQNDVGYGAYDLYDLGEFNQKGTVRTKYGTRSQLESAIHALKNNGVQV
SEQ ID NO: 9   (50)  GASQNDVGYGAYDLYDLGEFNQKGTIRTKYGTRNQLQAAVNALKSNGIQV
SEQ ID NO: 10  (50)  GASQNDVGYGAYDLYDLGEFNQKGTVRTKYGTRNQLQAAVTALKSNGIQV
SEQ ID NO: 11  (50)  GASQNDVGYGAYDLYDLGEFNQKGTVRTKYGTRSQLQAAVTSLKNNGIQV
SEQ ID NO: 12  (48)  GNSQADVGYGAYDLYDLGEFNQKGTVRTKYGTKAQLERAIGSLKSNDINV
SEQ ID NO: 13  (48)  GTSQADVGYGAYDLYDLGEFHQKGTVRTKYGTKGELQSAIKSLHSRDINV
SEQ ID NO: 14  (46)  AISQADVGYGAYDLYDLGEFHQKGTVRTKYGTKGELQSAIKSLHSRDINV 101                                              150
SEQ ID NO: 1   (98)  YGDVVINHKGGADATEDVTAVEVDPADRNRVISGEHLIKAWTHFHFPGRG
SEQ ID NO: 2   (99)  YADVVFDHKGGADGTEWVDAVEVNPSDRNQEISGTYQIQAWTKFDFPGRG
SEQ ID NO: 3  (101)  YADVVFNHKAGADGTEFVDAVEVDPSNRNQETSGTYQIQAWTKFDFPGRG
SEQ ID NO: 4   (98)  YADVVFNHKAGADGTELVDAVEVNPSDRNQEISGTYQIQAWTKFDFPGRG
SEQ ID NO: 5  (100)  YADVVFNHKAGADGTELVDAVEVNPSDRNQEISGTYQIQAWTKFDFPGRG
SEQ ID NO: 6   (96)  YGDVVLNHKAGADATEDVTAVEVNPANRNQETSEEYQIKAWTDFRFPGRG
SEQ ID NO: 7  (100)  YGDVVMNHKGGADGTEIVNAVEVNRSNRNQETSGEYAIEAWTKFDFPGRG
SEQ ID NO: 8  (100)  YGDVVMNHKGGADATENVLAVEVNPNNRNQEISGDYTIEAWTKFDFPGRG
SEQ ID NO: 9  (100)  YGDVVMNHKGGADATEMVRAVEVNPNNRNQEVSGEYTIEAWTKFDFPGRG
SEQ ID NO: 10 (100)  YGDVVMNHKGGADATEWVRAVEVNPSNRNQEVSGDYTIEAWTKFDFPGRG
SEQ ID NO: 11 (100)  YGDVVMNHKGGADATEMVRAVEVNPNNRNQEVTGEYTIEAWTRFDFPGRG
SEQ ID NO: 12  (98)  YGDVVMNHKMGADFTEAVQAVQVNPTNRWQDISGAYTIDAWTGFDFSGRN
SEQ ID NO: 13  (98)  YGDVVINHKGGADATEDVTAVEVDPADRNRVISGEYLIKAWTHFHFPGRG
SEQ ID NO: 14  (96)  YGDVVINHKAGADATEDVTAVEVDPADRNRVISGEHLIKAWTHFHFPGRG
```

Fig. 1

```
                        151                                           200
SEQ ID NO:  1   (148)   STYSDFKWHWYHFDGTDWDESR-KLNRIYKFQG--KAWDWEVSNENGNYD
SEQ ID NO:  2   (149)   NTYSSFKWRWYHFDGVDWDESR-KLSRIYKFRGIGKAWDWEVDTENGNYD
SEQ ID NO:  3   (151)   NTYSSFKWRWYHFDGTDWDESR-KLNRIYKFRSTGKAWDWEVDTENGNYD
SEQ ID NO:  4   (148)   NTYSSFKWRWYHFDGTDWDESR-KLNRIYKFRGTGKAWDWEVDTENGNYD
SEQ ID NO:  5   (150)   NTYSSFKWRWYHFDGTDWDESR-KLNRIYKFRGTGKAWDWEVDTENGNYD
SEQ ID NO:  6   (146)   NTYSDFKWHWYHFDGADWDESR-KISRIFKFRGEGKAWDWEVSSENGNYD
SEQ ID NO:  7   (150)   NNHSSFKWRWYHFDGTDWDQSRQLQNKIYKFRGTGKAWDWEVDTENGNYD
SEQ ID NO:  8   (150)   NTYSDFKWRWYHFDGVDWDQSRQFQNRIYKFRGDGKAWDWEVDSENGNYD
SEQ ID NO:  9   (150)   NTHSNFKWRWYHFDGVDWDQSRKLNNRIYKFRGDGKGWDWEVDTENGNYD
SEQ ID NO: 10   (150)   NTHSNFKWRWYHFDGVDWDQSRQLQNRIYKFRGDGKGWDWEVDTENGNYD
SEQ ID NO: 11   (150)   NTHSSFKWRWYHFDGVDWDQSRRLNNRIYKFRGHGKAWDWEVDTENGNYD
SEQ ID NO: 12   (148)   NAYSDFKWRWFHFNGVDWDQRY-QENHIFRFAN--TNWNWRVDEENGNYD
SEQ ID NO: 13   (148)   STYSDFKWYWYHFDGTDWDESR-KLNRIYKFQG--KYWDWEVSNENGNYD
SEQ ID NO: 14   (146)   STYSDFKWYWYHFDGTDWDESR-KLNRIYKFQG--KTWDWEVSNEFGNYD 201                                           250
SEQ ID NO:  1   (195)   YLMYADIDYDHPDVAAEIKRWGTWYANELQLDGFRLDAVKHIKFSFLRDW
SEQ ID NO:  2   (198)   YLMYADLDMDHPEVVTELKNWGKWYVNTTNIDGFRLDAVKHIKFSFFPDW
SEQ ID NO:  3   (200)   YLMFADLDMDHPEVVTELKNWGTWYVNTTNIDGFRLDAVKHIKYSFFPDW
SEQ ID NO:  4   (197)   YLMYADLDMDHPEVVSELKNWGKWYTTTNIDGFRLDAVKHIKYSFFPDW
SEQ ID NO:  5   (199)   YLMYADLDMDHPEVVSELKNWGKWYVITTNIDGFRLDAVKHIKYSFFPDW
SEQ ID NO:  6   (195)   YLMYADVDYDHPDVVAETKKWGIWYANELSLDGFRIDAAKHIKFSFLRDW
SEQ ID NO:  7   (200)   YLMYADVDMDHPEVIHELRNWGVWYTNTLNLDGFRIDAVKHIKYSFTRDW
SEQ ID NO:  8   (200)   YLMYADVDMDHPEVVNELRRWGEWYTNTLNLDGFRIDAVKHIKYSFTRDW
SEQ ID NO:  9   (200)   YLMYADIDMDHPEVVNELRNWGVWYTNTLGLDGFRIDAVKHIKYSFTRDW
SEQ ID NO: 10   (200)   YLMYADIDMDHPEVVNELRNWGVWYTNTLGLDGFRIDAVKHIKYSFTRDW
SEQ ID NO: 11   (200)   YLMYADIDMDHPEVVNELRNWGVWYTNTLGLDGFRIDAVKHIKYSFTRDW
SEQ ID NO: 12   (195)   YLLGSNIDFSHPEVQDELKDWGSWFTDELDLDGYRLDAIKHIPFWYTSDW
SEQ ID NO: 13   (195)   YLMYADIDYDHPDVVAEIKRWGTWYANELQLDGNRLDAVKHIKFSFLRDW
SEQ ID NO: 14   (193)   YLMYADFDYDHPDVVAEIKRWGTWYANELQLDGFRLDAVKHIKFSFLRDW 251                                           300
SEQ ID NO:  1   (245)   VNHVREKTGKEMFTVAEYWQNDLGALENYLNKTNFNHSVFDVPLHYQFHA
SEQ ID NO:  2   (248)   LSYVRSQTGKPLFTVGEYWSYDINKLHNYITKTNGTMSLFDAPLHNKFYT
SEQ ID NO:  3   (250)   LTYVRNQTGKNLFAVGEFWSYDVNKLHNYITKTNGSMSLFDAPLHNNFYT
SEQ ID NO:  4   (247)   LSYVRTQTQKPLFAVGEFWSYDISKLHNYITKTNGSMSLFDAPLHNNFYI
SEQ ID NO:  5   (249)   LSYLRTQTQKPLFAVGEFWSYDINKLHNYITKTNGSMSLFDAPLHNNFYI
SEQ ID NO:  6   (245)   VQAVRQATGKEMFTVAEYWQNNAGKLENYLNKTSFNQSVFDVPLHFNLQA
SEQ ID NO:  7   (250)   LTHVRNTTGKPMFAVAEFWKNDLGAIENYLNKTSWNHSVFDVPLHYNLYN
SEQ ID NO:  8   (250)   LTHVRNATGKEMFAVAEFWKNDLGALENYLNKTNWNHSVFDVPLHYNLYN
SEQ ID NO:  9   (250)   INHVRSATGKNMFAVAEFWKNDLGAIENYLNKTNWNHSVFDVPLHYNLYN
SEQ ID NO: 10   (250)   LTHVRNTTGKNMFAVAEFWKNDLGAIENYLSKTNWNHSVFDVPLHYNLYN
SEQ ID NO: 11   (250)   INHVRSATGKNMFAVAEFWKNDLGAIENYLQKTNWNHSVFDVPLHYNLYN
SEQ ID NO: 12   (245)   VRHQRNEADQDLFVVGEYWKDDVGALEFYLDEMNWEMSLFDVPLNYNFYR
SEQ ID NO: 13   (245)   VNHVREKTGKEMFTVAEYWQNDLGALENYLNKTNFNHSVFDVPLHYQFYA
SEQ ID NO: 14   (243)   VNHVREKTGKEMFTVAEYWSNDLGALENYLNKTNFNHSVFDVPLHYQFHA
```

Fig. 1 cont.

```
                  301                                                350
SEQ ID NO: 1   (295) ASTQGGGYDMRKLLNGTVVSKHPLKSVTFVDNHDTQPGQSLESTVQTWFK
SEQ ID NO: 2   (298) ASKSGGAFDMRTLMTNTLMKDQPTLAVTFVDNHDTEPGQALQSWVDPWFK
SEQ ID NO: 3   (300) ASKSSGYFDMRYLLNNTLMKDQPSLAVTLVDNHDTQPGQSLQSWVEPWFK
SEQ ID NO: 4   (297) ASKSSGGYFDMRTLLNNTLMKDQPTLAVTLVDNHDTEPGQSLQSWVEPWFK
SEQ ID NO: 5   (299) ASKSGGYFDMRTLLNNTLMKEQPTLSVTLVDNHDTEPGQSLQSWVEPWFK
SEQ ID NO: 6   (295) ASSQGGGYDMRRLLDGTVVSRHPEKAVTFVENHDTQPGQSLESTVQTWFK
SEQ ID NO: 7   (300) ASNSGGYYDMRNILNGSVVQKHPTHAVTFVDNHDSQPGEALESFVQQWFK
SEQ ID NO: 8   (300) ASNSGGNYDMAKLLNGTVVQKHPMHAVTFVDNHDSQPGESLESFVQEWFK
SEQ ID NO: 9   (300) ASKSGGNYDMRQIFNGTVVQRHPMHAVTFVDNHDSQPEEALESFVEEWFK
SEQ ID NO: 10  (300) ASRSGGNYDMRQIFNGTVVQRHPTHAVTFVDNHDSQPEEALESFVEEWFK
SEQ ID NO: 11  (300) ASKSGGNYDMRNIFNGTVVQRHPSHAVTFVDNHDSQPEEALESFVEEWFK
SEQ ID NO: 12  (295) ASQQGGSYDMRNILRGSLVEAHPMHAVTFVDNHDTQPGESLESWVADWFK
SEQ ID NO: 13  (295) ASTQGGGYDMRKLLNDTVVSKHPLKSVTFVDNHDTQPGQSLESTVQTWFK
SEQ ID NO: 14  (293) ASTQGGGYDMRKLLNGTVVSKHPLKSVTFVDNHDTQPGQSLESTVQTWFK 351                                                400
SEQ ID NO: 1   (345) PLAYAFILTRESGYPQVFYGDMYGTKGDSQREIPALKHKIEPILKARKQY
SEQ ID NO: 2   (348) PLAYAFILTRQEGYPCVFYGDYYGIPQYN---IPSLKSKIDPLLIARRDY
SEQ ID NO: 3   (350) PLAYAFILTRQEGYPCVFYGDYYGIPKYN---IPGLKSKIDPLLIARRDY
SEQ ID NO: 4   (347) PLAYAFILTRQEGYPCVFYGDYYGIPKYN---IPALKSKLDPLLIARRDY
SEQ ID NO: 5   (349) PLAYAFILTRQEGYPCVFYGDYYGIPKYN---IPALKSKLDPLLIARRDY
SEQ ID NO: 6   (345) PLAYAFILTRESGYPQVFYGDMYGTKGTSPKEIPSLKDNIEPILKARKEY
SEQ ID NO: 7   (350) PLAYALVLTREQGYPSVFYGDYYGIPTHG---VPAMKSKIDPLLQARQTF
SEQ ID NO: 8   (350) PLAYALILTREQGYPSVFYGDYYGIPTHS---VPAMKAKIDPILEARQNF
SEQ ID NO: 9   (350) PLAYALTLTREQGYPSVFYGDYYGIPTHG---VPAMKSKIDPILEARQKY
SEQ ID NO: 10  (350) PLACALTLTRDQGYPSVFYGDYYGIPTHG---VPAMKSKIDPILEARQKY
SEQ ID NO: 11  (350) PLAYALTLTREQGYPSVFYGDYYGIPTHG---VPAMRSKIDPILEARQKY
SEQ ID NO: 12  (345) PLAYATILTREGGYPNVFYGDYYGIPNDN---ISAKKDMIDELLDARQNY
SEQ ID NO: 13  (345) PLAYAFILTRESGYPQVFYGDMYGTKGDSQREIPALKHKIEPILKARKQY
SEQ ID NO: 14  (343) PLAYAFILTRESGYPQVFYGDMYGTKGDSQREIPALKHKIEPILKARKQY 401                                                450
SEQ ID NO: 1   (395) AYGAQHDYFDHHDIVGWTREGDSSVANSGLAALITDGPGGAKRMYVGRQN
SEQ ID NO: 2   (395) AYGTQHDYLDHSDIIGWTREGVTEKPGSGLAALITDGPGGSKWMYVGKQH
SEQ ID NO: 3   (397) AYGTQRDYIDHQDIIGWTREGIDTKPNSGLAALITDGPGGSKWMYVGKKH
SEQ ID NO: 4   (394) AYGTQHDYIDSADIIGWTREGVAEKANSGLAALITDGPGGSKWMYVGKQH
SEQ ID NO: 5   (396) AYGTQHDYIDNADIIGWTREGVAEKANSGLAALITDGPGGSKWMYVGKQH
SEQ ID NO: 6   (395) AYGPQHDYIDHPDVIGWTREGDSSAAKSGLAALITDGPGGSKRMYAGLKN
SEQ ID NO: 7   (397) AYGTQHDYFDHHDIIGWTREGNSSHPNSGLATIMSDGPGGNKWMYVGKNK
SEQ ID NO: 8   (397) AYGTQHDYFDHHNIIGWTREGNTTHPNSGLATIMSDGPGGEKWMYVGQNK
SEQ ID NO: 9   (397) AYGRQNDYLDHHNIIGWTREGNTAHPNSGLATIMSDGAGGNKWMFVGRNK
SEQ ID NO: 10  (397) AYGKQNDYLDHHNMIGWTREGNTAHPNSGLATIMSDGPGGNKWMFVGRNK
SEQ ID NO: 11  (397) AYGKQNDYLDHHNIIGWTREGNTAHPNSGLATIMSDGAGGSKWMFVGRNK
SEQ ID NO: 12  (392) AYGTQHDYFDHWDVVGWTREGSSSRPNSGLATIMSNGPGGSKWMYVGRQN
SEQ ID NO: 13  (395) AYGAQHDYFDHHDIVGWTREGDSSVANSGLAALITDGPGGAKRMYVGRQN
SEQ ID NO: 14  (393) AYGAQHDYFDHHDIVGWTREGDSSVANSGLAALITDGPGGAKRMYVGRQN
```

Fig. 1 cont.

```
              451                                               500
SEQ ID NO: 1  (445) AGETWHDITGNRSEPVVINSEGWGEFHVNGGSVSIYVQR-----------
SEQ ID NO: 2  (445) AGKVFYDLTGNRSDTVTINSDGWGEFKVNGGSVSVWVPRKTT---VSTIA
SEQ ID NO: 3  (447) AGKVFYDLTGNRSDTVTINADGWGEFKVNGGSVSIWVAKTSN---VTFTV
SEQ ID NO: 4  (444) AGKTFYDLTGNRSDTVTINADGWGEFKVNGGSVSIWVPKISTTSQITFTV
SEQ ID NO: 5  (446) AGKTFYDLTGNRSDTVTINADGWGEFKVNGGSVSIWVPKTSTTSQITFTV
SEQ ID NO: 6  (445) AGETWYDITGNRSDTVKIGSDGWGEFHVNDGSVSIYVQK-----------
SEQ ID NO: 7  (447) AGQVWRDITGNRTGTVTINADGWGNFSVNGGSVSVWVKQ-----------
SEQ ID NO: 8  (447) AGQVWHDITGNKPGTVTINADGWANFSVNGGSVSIWVKR-----------
SEQ ID NO: 9  (447) AGQVWTDITGNRAGTVTINADGWGNFSVNGGSVSIWVNK-----------
SEQ ID NO: 10 (447) AGQVWRDITGNRSGTVTINADGWGNFSVNGGSVSIWVNN-----------
SEQ ID NO: 11 (447) AGQVWSDITGNRTGTVTINADGWANFSVNGGSVSIWVNK-----------
SEQ ID NO: 12 (442) AGQTWTDLTGNNGASVTINGDGWGEFFTNGGSVSVYVNQ-----------
SEQ ID NO: 13 (445) AGETWYDITGNRSEPVVINSEGWGEFHVNDGSVSIYVQR-----------
SEQ ID NO: 14 (443) AGETWHDITGNRSEPVVINSEGWGEFHVNGGSVSIYVQR-----------

501                                               550
SEQ ID NO: 1  (484) --------------------------------------------------
SEQ ID NO: 2  (492) RPITTRPWTGEFVRWTEPRLVAWP--------------------------
SEQ ID NO: 3  (494) NNATTTSGQNVYVVANIPELGNWNTANAIKMNPSSYPTWKATIALPQGKA
SEQ ID NO: 4  (494) NNATTVWGQNVYVVGNISQLGNWDPVHAVQMTPSSYPTWTVTIPLLQGQN
SEQ ID NO: 5  (496) NNATTVWGQNVYVVGNISQLGNWDPVNAVQMTPSSYPTWVVTVPLPQSQN
SEQ ID NO: 6  (484) --------------------------------------------------
SEQ ID NO: 7  (486) --------------------------------------------------
SEQ ID NO: 8  (486) --------------------------------------------------
SEQ ID NO: 9  (486) --------------------------------------------------
SEQ ID NO: 10 (486) --------------------------------------------------
SEQ ID NO: 11 (486) --------------------------------------------------
SEQ ID NO: 12 (481) --------------------------------------------------
SEQ ID NO: 13 (484) --------------------------------------------------
SEQ ID NO: 14 (482) --------------------------------------------------

551                                     591
SEQ ID NO: 1  (484) -----------------------------------------
SEQ ID NO: 2  (516) -----------------------------------------
SEQ ID NO: 3  (544) IEFKFIKKDQAGNVIWESTSNRTYTVPFSSTGSYTASWNVP
SEQ ID NO: 4  (544) IQFKFIKKDSAGNVIWEDISNRTYTVPTAASGAYTASWNVP
SEQ ID NO: 5  (546) IQFKFIKKDGSGNVIWENISNRTYTVPTAASGAYTANWNVP
SEQ ID NO: 6  (484) -----------------------------------------
SEQ ID NO: 7  (486) -----------------------------------------
SEQ ID NO: 8  (486) -----------------------------------------
SEQ ID NO: 9  (486) -----------------------------------------
SEQ ID NO: 10 (486) -----------------------------------------
SEQ ID NO: 11 (486) -----------------------------------------
SEQ ID NO: 12 (481) -----------------------------------------
SEQ ID NO: 13 (484) -----------------------------------------
SEQ ID NO: 14 (482) -----------------------------------------
```

Fig. 1 cont.

SEQUENCE LISTING

```
<160> NUMBER OF SEQ ID NOS: 14

<210> SEQ ID NO 1
<211> LENGTH: 483
<212> TYPE: PRT
<213> ORGANISM: Bacillus licheniformis

<400> SEQUENCE: 1

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160
```

Asp Gly Thr Asp Trp Asp Glu Ser Arg Lys Leu Asn Arg Ile Tyr Lys
            165                 170                 175

Phe Gln Gly Lys Ala Trp Asp Trp Glu Val Ser Asn Glu Asn Gly Asn
        180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
        260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
        290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
        340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
        370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
        420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
        450                 455                 460

Glu Gly Trp Gly Glu Phe His Val Asn Gly Gly Ser Val Ser Ile Tyr
465                 470                 475                 480

Val Gln Arg

<210> SEQ ID NO 2
<211> LENGTH: 515
<212> TYPE: PRT
<213> ORGANISM: Bacillus stearothermophilus

<400> SEQUENCE: 2

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
        35                  40                  45

```
Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
            195                 200                 205

Pro Glu Val Val Thr Glu Leu Lys Asn Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
            275                 280                 285

Ala Pro Leu His Asn Lys Phe Tyr Thr Ala Ser Lys Ser Gly Gly Ala
290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
```

```
                465                 470                 475                 480
Val Pro Arg Lys Thr Thr Val Ser Thr Ile Ala Arg Pro Ile Thr Thr
                485                 490                 495
Arg Pro Trp Thr Gly Glu Phe Val Arg Trp Thr Glu Pro Arg Leu Val
                500                 505                 510
Ala Trp Pro
        515

<210> SEQ ID NO 3
<211> LENGTH: 584
<212> TYPE: PRT
<213> ORGANISM: Bacillus species

<400> SEQUENCE: 3

Ala Asn Thr Ala Pro Ile Asn Glu Thr Met Met Gln Tyr Phe Glu Trp
1               5                   10                  15
Asp Leu Pro Asn Asp Gly Thr Leu Trp Thr Lys Val Lys Asn Glu Ala
                20                  25                  30
Ala Asn Leu Ser Ser Leu Gly Ile Thr Ala Leu Trp Leu Pro Pro Ala
            35                  40                  45
Tyr Lys Gly Thr Ser Gln Ser Asp Val Gly Tyr Gly Val Tyr Asp Leu
        50                  55                  60
Tyr Asp Leu Gly Glu Phe Asn Gln Lys Gly Thr Ile Arg Thr Lys Tyr
65                  70                  75                  80
Gly Thr Lys Thr Gln Tyr Ile Gln Ala Ile Gln Ala Ala Lys Ala Ala
                85                  90                  95
Gly Met Gln Val Tyr Ala Asp Val Val Phe Asn His Lys Ala Gly Ala
            100                 105                 110
Asp Gly Thr Glu Phe Val Asp Ala Val Glu Val Asp Pro Ser Asn Arg
        115                 120                 125
Asn Gln Glu Thr Ser Gly Thr Tyr Gln Ile Gln Ala Trp Thr Lys Phe
130                 135                 140
Asp Phe Pro Gly Arg Gly Asn Thr Tyr Ser Ser Phe Lys Trp Arg Trp
145                 150                 155                 160
Tyr His Phe Asp Gly Thr Asp Trp Asp Glu Ser Arg Lys Leu Asn Arg
                165                 170                 175
Ile Tyr Lys Phe Arg Ser Thr Gly Lys Ala Trp Asp Trp Glu Val Asp
            180                 185                 190
Thr Glu Asn Gly Asn Tyr Asp Tyr Leu Met Phe Ala Asp Leu Asp Met
        195                 200                 205
Asp His Pro Glu Val Val Thr Glu Leu Lys Asn Trp Gly Thr Trp Tyr
210                 215                 220
Val Asn Thr Thr Asn Ile Asp Gly Phe Arg Leu Asp Ala Val Lys His
225                 230                 235                 240
Ile Lys Tyr Ser Phe Phe Pro Asp Trp Leu Thr Tyr Val Arg Asn Gln
                245                 250                 255
Thr Gly Lys Asn Leu Phe Ala Val Gly Glu Phe Trp Ser Tyr Asp Val
            260                 265                 270
Asn Lys Leu His Asn Tyr Ile Thr Lys Thr Asn Gly Ser Met Ser Leu
        275                 280                 285
Phe Asp Ala Pro Leu His Asn Asn Phe Tyr Thr Ala Ser Lys Ser Ser
290                 295                 300
Gly Tyr Phe Asp Met Arg Tyr Leu Leu Asn Asn Thr Leu Met Lys Asp
305                 310                 315                 320
```

```
Gln Pro Ser Leu Ala Val Thr Leu Val Asp Asn His Asp Thr Gln Pro
                325                 330                 335

Gly Gln Ser Leu Gln Ser Trp Val Glu Pro Trp Phe Lys Pro Leu Ala
            340                 345                 350

Tyr Ala Phe Ile Leu Thr Arg Gln Glu Gly Tyr Pro Cys Val Phe Tyr
        355                 360                 365

Gly Asp Tyr Tyr Gly Ile Pro Lys Tyr Asn Ile Pro Gly Leu Lys Ser
    370                 375                 380

Lys Ile Asp Pro Leu Leu Ile Ala Arg Arg Asp Tyr Ala Tyr Gly Thr
385                 390                 395                 400

Gln Arg Asp Tyr Ile Asp His Gln Asp Ile Ile Gly Trp Thr Arg Glu
                405                 410                 415

Gly Ile Asp Thr Lys Pro Asn Ser Gly Leu Ala Ala Leu Ile Thr Asp
            420                 425                 430

Gly Pro Gly Gly Ser Lys Trp Met Tyr Val Gly Lys Lys His Ala Gly
        435                 440                 445

Lys Val Phe Tyr Asp Leu Thr Gly Asn Arg Ser Asp Thr Val Thr Ile
    450                 455                 460

Asn Ala Asp Gly Trp Gly Glu Phe Lys Val Asn Gly Gly Ser Val Ser
465                 470                 475                 480

Ile Trp Val Ala Lys Thr Ser Asn Val Thr Phe Thr Val Asn Asn Ala
                485                 490                 495

Thr Thr Thr Ser Gly Gln Asn Val Tyr Val Val Ala Asn Ile Pro Glu
            500                 505                 510

Leu Gly Asn Trp Asn Thr Ala Asn Ala Ile Lys Met Asn Pro Ser Ser
        515                 520                 525

Tyr Pro Thr Trp Lys Ala Thr Ile Ala Leu Pro Gln Gly Lys Ala Ile
    530                 535                 540

Glu Phe Lys Phe Ile Lys Lys Asp Gln Ala Gly Asn Val Ile Trp Glu
545                 550                 555                 560

Ser Thr Ser Asn Arg Thr Tyr Thr Val Pro Phe Ser Ser Thr Gly Ser
                565                 570                 575

Tyr Thr Ala Ser Trp Asn Val Pro
            580

<210> SEQ ID NO 4
<211> LENGTH: 584
<212> TYPE: PRT
<213> ORGANISM: Bacillus flavothermus

<400> SEQUENCE: 4

Val Pro Val Asn Gly Thr Met Met Gln Tyr Phe Glu Trp Tyr Leu Pro
1               5                   10                  15

Asp Asp Gly Thr Leu Trp Thr Lys Val Ala Asn Ala Gln Ser Leu
            20                  25                  30

Ala Asn Leu Gly Ile Thr Ala Leu Trp Leu Pro Pro Ala Tyr Lys Gly
        35                  40                  45

Thr Ser Ser Ser Asp Val Gly Tyr Gly Val Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Thr Gln Tyr Ile Gln Ala Ile Gln Ala Ala His Thr Ala Gly Met Gln
                85                  90                  95

Val Tyr Ala Asp Val Val Phe Asn His Lys Ala Gly Ala Asp Gly Thr
            100                 105                 110
```

```
Glu Leu Val Asp Ala Val Glu Val Asn Pro Ser Asp Arg Asn Gln Glu
            115                 120                 125

Ile Ser Gly Thr Tyr Gln Ile Gln Ala Trp Thr Lys Phe Asp Phe Pro
            130                 135                 140

Gly Arg Gly Asn Thr Tyr Ser Ser Phe Lys Trp Arg Trp Tyr His Phe
145                 150                 155                 160

Asp Gly Thr Asp Trp Asp Glu Ser Arg Lys Leu Asn Arg Ile Tyr Lys
                165                 170                 175

Phe Arg Gly Thr Gly Lys Ala Trp Asp Trp Glu Val Asp Thr Glu Asn
                180                 185                 190

Gly Asn Tyr Asp Tyr Leu Met Tyr Ala Asp Leu Asp Met Asp His Pro
            195                 200                 205

Glu Val Val Ser Glu Leu Lys Asn Trp Gly Lys Trp Tyr Val Thr Thr
            210                 215                 220

Thr Asn Ile Asp Gly Phe Arg Leu Asp Ala Val Lys His Ile Lys Tyr
225                 230                 235                 240

Ser Phe Phe Pro Asp Trp Leu Ser Tyr Val Arg Thr Gln Thr Gln Lys
                245                 250                 255

Pro Leu Phe Ala Val Gly Glu Phe Trp Ser Tyr Asp Ile Ser Lys Leu
            260                 265                 270

His Asn Tyr Ile Thr Lys Thr Asn Gly Ser Met Ser Leu Phe Asp Ala
            275                 280                 285

Pro Leu His Asn Asn Phe Tyr Ile Ala Ser Lys Ser Gly Gly Tyr Phe
            290                 295                 300

Asp Met Arg Thr Leu Leu Asn Asn Thr Leu Met Lys Asp Gln Pro Thr
305                 310                 315                 320

Leu Ala Val Thr Leu Val Asp Asn His Asp Thr Glu Pro Gly Gln Ser
                325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Lys Tyr Asn Ile Pro Ala Leu Lys Ser Lys Leu Asp
370                 375                 380

Pro Leu Leu Ile Ala Arg Arg Asp Tyr Ala Tyr Gly Thr Gln His Asp
385                 390                 395                 400

Tyr Ile Asp Ser Ala Asp Ile Ile Gly Trp Thr Arg Glu Gly Val Ala
                405                 410                 415

Glu Lys Ala Asn Ser Gly Leu Ala Ala Leu Ile Thr Asp Gly Pro Gly
            420                 425                 430

Gly Ser Lys Trp Met Tyr Val Gly Lys Gln His Ala Gly Lys Thr Phe
            435                 440                 445

Tyr Asp Leu Thr Gly Asn Arg Ser Asp Thr Val Thr Ile Asn Ala Asp
            450                 455                 460

Gly Trp Gly Glu Phe Lys Val Asn Gly Gly Ser Val Ser Ile Trp Val
465                 470                 475                 480

Pro Lys Ile Ser Thr Thr Ser Gln Ile Thr Phe Thr Val Asn Asn Ala
                485                 490                 495

Thr Thr Val Trp Gly Gln Asn Val Tyr Val Val Gly Asn Ile Ser Gln
            500                 505                 510

Leu Gly Asn Trp Asp Pro Val His Ala Val Gln Met Thr Pro Ser Ser
            515                 520                 525
```

Tyr Pro Thr Trp Thr Val Thr Ile Pro Leu Leu Gln Gly Gln Asn Ile
                530                 535                 540

Gln Phe Lys Phe Ile Lys Lys Asp Ser Ala Gly Asn Val Ile Trp Glu
545                 550                 555                 560

Asp Ile Ser Asn Arg Thr Tyr Thr Val Pro Thr Ala Ala Ser Gly Ala
                565                 570                 575

Tyr Thr Ala Ser Trp Asn Val Pro
            580

<210> SEQ ID NO 5
<211> LENGTH: 586
<212> TYPE: PRT
<213> ORGANISM: Bacillus species

<400> SEQUENCE: 5

Gly Ser Val Pro Val Asn Gly Thr Met Met Gln Tyr Phe Glu Trp Tyr
1               5                   10                  15

Leu Pro Asp Asp Gly Thr Leu Trp Thr Lys Val Ala Asn Asn Ala Gln
                20                  25                  30

Ser Leu Ala Asn Leu Gly Ile Thr Ala Leu Trp Leu Pro Pro Ala Tyr
            35                  40                  45

Lys Gly Thr Ser Ser Asp Val Gly Tyr Gly Val Tyr Asp Leu Tyr
    50                  55                  60

Asp Leu Gly Glu Phe Asn Gln Lys Gly Thr Val Arg Thr Lys Tyr Gly
65                  70                  75                  80

Thr Lys Thr Gln Tyr Ile Gln Ala Ile Gln Ala Ala His Thr Ala Gly
                85                  90                  95

Met Gln Val Tyr Ala Asp Val Val Phe Asn His Lys Ala Gly Ala Asp
                100                 105                 110

Gly Thr Glu Leu Val Asp Ala Val Glu Val Asn Pro Ser Asp Arg Asn
            115                 120                 125

Gln Glu Ile Ser Gly Thr Tyr Gln Ile Gln Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Thr Gly Lys Ala Trp Asp Trp Glu Val Asp Thr
            180                 185                 190

Glu Asn Gly Asn Tyr Asp Tyr Leu Met Tyr Ala Asp Leu Asp Met Asp
        195                 200                 205

His Pro Glu Val Val Ser Glu Leu Lys Asn Trp Gly Lys Trp Tyr Val
    210                 215                 220

Ile Thr Thr Asn Ile Asp Gly Phe Arg Leu Asp Ala Val Lys His Ile
225                 230                 235                 240

Lys Tyr Ser Phe Phe Pro Asp Trp Leu Ser Tyr Leu Arg Thr Gln Thr
                245                 250                 255

Gln Lys Pro Leu Phe Ala Val Gly Glu Phe Trp Ser Tyr Asp Ile Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Ile Ala Ser Lys Ser Gly Gly
    290                 295                 300

Tyr Phe Asp Met Arg Thr Leu Leu Asn Asn Thr Leu Met Lys Glu Gln
305                 310                 315                 320

```
Pro Thr Leu Ser Val Thr Leu Val Asp Asn His Asp Thr Glu Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
        355                 360                 365

Asp Tyr Tyr Gly Ile Pro Lys Tyr Asn Ile Pro Ala Leu Lys Ser Lys
    370                 375                 380

Leu Asp Pro Leu Leu Ile Ala Arg Arg Asp Tyr Ala Tyr Gly Thr Gln
385                 390                 395                 400

His Asp Tyr Ile Asp Asn Ala Asp Ile Ile Gly Trp Thr Arg Glu Gly
                405                 410                 415

Val Ala Glu Lys Ala Asn Ser Gly Leu Ala Ala Leu Ile Thr Asp Gly
            420                 425                 430

Pro Gly Gly Ser Lys Trp Met Tyr Val Gly Lys Gln His Ala Gly Lys
        435                 440                 445

Thr Phe Tyr Asp Leu Thr Gly Asn Arg Ser Asp Thr Val Thr Ile Asn
    450                 455                 460

Ala Asp Gly Trp Gly Glu Phe Lys Val Asn Gly Gly Ser Val Ser Ile
465                 470                 475                 480

Trp Val Pro Lys Thr Ser Thr Ser Gln Ile Thr Phe Thr Val Asn
                485                 490                 495

Asn Ala Thr Thr Val Trp Gly Gln Asn Val Tyr Val Gly Asn Ile
            500                 505                 510

Ser Gln Leu Gly Asn Trp Asp Pro Val Asn Ala Val Gln Met Thr Pro
        515                 520                 525

Ser Ser Tyr Pro Thr Trp Val Val Thr Val Pro Leu Pro Gln Ser Gln
    530                 535                 540

Asn Ile Gln Phe Lys Phe Ile Lys Lys Asp Gly Ser Gly Asn Val Ile
545                 550                 555                 560

Trp Glu Asn Ile Ser Asn Arg Thr Tyr Thr Val Pro Thr Ala Ala Ser
                565                 570                 575

Gly Ala Tyr Thr Ala Asn Trp Asn Val Pro
            580                 585

<210> SEQ ID NO 6
<211> LENGTH: 483
<212> TYPE: PRT
<213> ORGANISM: Bacillus amyloliquefaciens

<400> SEQUENCE: 6

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
        35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
```

-continued

```
                100                 105                 110
        Val Thr Ala Val Glu Val Asn Pro Ala Asn Arg Asn Gln Glu Thr Ser
                    115                 120                 125
        Glu Glu Tyr Gln Ile Lys Ala Trp Thr Asp Phe Arg Phe Pro Gly Arg
                130                 135                 140
        Gly Asn Thr Tyr Ser Asp Phe Lys Trp His Trp Tyr His Phe Asp Gly
        145                 150                 155                 160
        Ala Asp Trp Asp Glu Ser Arg Lys Ile Ser Arg Ile Phe Lys Phe Arg
                        165                 170                 175
        Gly Glu Gly Lys Ala Trp Asp Trp Glu Val Ser Ser Glu Asn Gly Asn
                    180                 185                 190
        Tyr Asp Tyr Leu Met Tyr Ala Asp Val Asp Tyr Asp His Pro Asp Val
                195                 200                 205
        Val Ala Glu Thr Lys Lys Trp Gly Ile Trp Tyr Ala Asn Glu Leu Ser
            210                 215                 220
        Leu Asp Gly Phe Arg Ile Asp Ala Ala Lys His Ile Lys Phe Ser Phe
        225                 230                 235                 240
        Leu Arg Asp Trp Val Gln Ala Val Arg Gln Ala Thr Gly Lys Glu Met
                        245                 250                 255
        Phe Thr Val Ala Glu Tyr Trp Gln Asn Asn Ala Gly Lys Leu Glu Asn
                    260                 265                 270
        Tyr Leu Asn Lys Thr Ser Phe Asn Gln Ser Val Phe Asp Val Pro Leu
                275                 280                 285
        His Phe Asn Leu Gln Ala Ala Ser Ser Gln Gly Gly Gly Tyr Asp Met
            290                 295                 300
        Arg Arg Leu Leu Asp Gly Thr Val Val Ser Arg His Pro Glu Lys Ala
        305                 310                 315                 320
        Val Thr Phe Val Glu Asn His Asp Thr Gln Pro Gly Gln Ser Leu Glu
                        325                 330                 335
        Ser Thr Val Gln Thr Trp Phe Lys Pro Leu Ala Tyr Ala Phe Ile Leu
                    340                 345                 350
        Thr Arg Glu Ser Gly Tyr Pro Gln Val Phe Tyr Gly Asp Met Tyr Gly
                355                 360                 365
        Thr Lys Gly Thr Ser Pro Lys Glu Ile Pro Ser Leu Lys Asp Asn Ile
            370                 375                 380
        Glu Pro Ile Leu Lys Ala Arg Lys Glu Tyr Ala Tyr Gly Pro Gln His
        385                 390                 395                 400
        Asp Tyr Ile Asp His Pro Asp Val Ile Gly Trp Thr Arg Glu Gly Asp
                        405                 410                 415
        Ser Ser Ala Ala Lys Ser Gly Leu Ala Ala Leu Ile Thr Asp Gly Pro
                    420                 425                 430
        Gly Gly Ser Lys Arg Met Tyr Ala Gly Leu Lys Asn Ala Gly Glu Thr
                435                 440                 445
        Trp Tyr Asp Ile Thr Gly Asn Arg Ser Asp Thr Val Lys Ile Gly Ser
            450                 455                 460
        Asp Gly Trp Gly Glu Phe His Val Asn Asp Gly Ser Val Ser Ile Tyr
        465                 470                 475                 480
        Val Gln Lys

<210> SEQ ID NO 7
<211> LENGTH: 485
<212> TYPE: PRT
<213> ORGANISM: Bacillus species
```

```
<400> SEQUENCE: 7

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Ala Trp
        35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ser Leu Lys Asn Asn Gly
            85                  90                  95

Ile Gln Val Tyr Gly Asp Val Val Met Asn His Lys Gly Gly Ala Asp
            100                 105                 110

Gly Thr Glu Ile Val Asn Ala Val Glu Val Asn Arg Ser Asn Arg Asn
            115                 120                 125

Gln Glu Thr Ser Gly Glu Tyr Ala Ile Glu Ala Trp Thr Lys Phe Asp
130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
            165                 170                 175

Ile Tyr Lys Phe Arg Gly Thr Gly Lys Ala Trp Asp Trp Glu Val Asp
            180                 185                 190

Thr Glu Asn Gly Asn Tyr Asp Tyr Leu Met Tyr Ala Asp Val Asp Met
            195                 200                 205

Asp His Pro Glu Val Ile His Glu Leu Arg Asn Trp Gly Val Trp Tyr
210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Thr
            245                 250                 255

Thr Gly Lys Pro Met Phe Ala Val Ala Glu Phe Trp Lys Asn Asp Leu
            260                 265                 270

Gly Ala Ile Glu Asn Tyr Leu Asn Lys Thr Ser Trp Asn His Ser Val
            275                 280                 285

Phe Asp Val Pro Leu His Tyr Asn Leu Tyr Asn Ala Ser Asn Ser Gly
290                 295                 300

Gly Tyr Tyr Asp Met Arg Asn Ile Leu Asn Gly Ser Val Val Gln Lys
305                 310                 315                 320

His Pro Thr His Ala Val Thr Phe Val Asp Asn His Asp Ser Gln Pro
            325                 330                 335

Gly Glu Ala Leu Glu Ser Phe Val Gln Gln Trp Phe Lys Pro Leu Ala
            340                 345                 350

Tyr Ala Leu Val Leu Thr Arg Glu Gln Gly Tyr Pro Ser Val Phe Tyr
            355                 360                 365

Gly Asp Tyr Tyr Gly Ile Pro Thr His Gly Val Pro Ala Met Lys Ser
370                 375                 380

Lys Ile Asp Pro Leu Leu Gln Ala Arg Gln Thr Phe Ala Tyr Gly Thr
385                 390                 395                 400

Gln His Asp Tyr Phe Asp His His Asp Ile Ile Gly Trp Thr Arg Glu
            405                 410                 415
```

Gly Asn Ser Ser His Pro Asn Ser Gly Leu Ala Thr Ile Met Ser Asp
                420                 425                 430

Gly Pro Gly Gly Asn Lys Trp Met Tyr Val Gly Lys Asn Lys Ala Gly
            435                 440                 445

Gln Val Trp Arg Asp Ile Thr Gly Asn Arg Thr Gly Thr Val Thr Ile
450                 455                 460

Asn Ala Asp Gly Trp Gly Asn Phe Ser Val Asn Gly Gly Ser Val Ser
465                 470                 475                 480

Val Trp Val Lys Gln
            485

<210> SEQ ID NO 8
<211> LENGTH: 485
<212> TYPE: PRT
<213> ORGANISM: Bacillus halmapalus

<400> SEQUENCE: 8

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
                20                  25                  30

Asn Leu Arg Asn Arg Gly Ile Thr Ala Ile Trp Ile Pro Pro Ala Trp
            35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125

Gln Glu Ile Ser Gly Asp Tyr Thr Ile Glu Ala Trp Thr Lys Phe Asp
    130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
        195                 200                 205

Asp His Pro Glu Val Val Asn Glu Leu Arg Arg Trp Gly Glu Trp Tyr
    210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
        275                 280                 285

Phe Asp Val Pro Leu His Tyr Asn Leu Tyr Asn Ala Ser Asn Ser Gly

```
                   290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Ser Val Pro Ala Met Lys Ala
    370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
        435                 440                 445

Gln Val Trp His Asp Ile Thr Gly Asn Lys Pro Gly Thr Val Thr Ile
    450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 9
<211> LENGTH: 485
<212> TYPE: PRT
<213> ORGANISM: Bacillus species

<400> SEQUENCE: 9

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
                20                  25                  30

Asn Leu Lys Asp Lys Gly Ile Ser Ala Val Trp Ile Pro Pro Ala Trp
            35                  40                  45

Lys Gly Ala Ser Gln Asn Asp Val Gly Tyr Gly Ala Tyr Asp Leu Tyr
        50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175
```

```
Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Asn Lys Trp Met Phe Val Gly Arg Asn Lys Ala Gly
        435                 440                 445

Gln Val Trp Thr Asp Ile Thr Gly Asn Arg Ala Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 10
<211> LENGTH: 485
<212> TYPE: PRT
<213> ORGANISM: Bacillus species

<400> SEQUENCE: 10

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60
```

```
Asp Leu Gly Glu Phe Asn Gln Lys Gly Thr Val Arg Thr Lys Tyr Gly
 65                  70                  75                  80

Thr Arg Asn Gln Leu Gln Ala Ala Val Thr Ala Leu Lys Ser Asn Gly
             85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Asn Met Phe Ala Val Ala Glu Phe Trp Lys Asn Asp Ile
            260                 265                 270

Gly Ala Ile Glu Asn Tyr Leu Ser Lys Thr Asn Trp Asn His Ser Val
        275                 280                 285

Phe Asp Val Pro Leu His Tyr Asn Leu Tyr Asn Ala Ser Arg Ser Gly
    290                 295                 300

Gly Asn Tyr Asp Met Arg Gln Ile Phe Asn Gly Thr Val Val Gln Arg
305                 310                 315                 320

His Pro Thr His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Cys Ala Leu Thr Leu Thr Arg Asp Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Met Ile Gly Trp Thr Arg Glu
                405                 410                 415

Gly Asn Thr Ala His Pro Asn Ser Gly Leu Ala Thr Ile Met Ser Asp
            420                 425                 430

Gly Pro Gly Gly Asn Lys Trp Met Tyr Val Gly Arg Asn Lys Ala Gly
        435                 440                 445

Gln Val Trp Arg Asp Ile Thr Gly Asn Arg Ser Gly Thr Val Thr Ile
    450                 455                 460

Asn Ala Asp Gly Trp Gly Asn Phe Ser Val Asn Gly Gly Ser Val Ser
465                 470                 475                 480
```

Ile Trp Val Asn Asn
            485

<210> SEQ ID NO 11
<211> LENGTH: 485
<212> TYPE: PRT
<213> ORGANISM: Bacillus species

<400> SEQUENCE: 11

His His Asn Gly Thr Asn Gly Thr Met Met Gln Tyr Tyr Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

```
Gly Asp Tyr Tyr Gly Ile Pro Thr His Gly Val Pro Ala Met Arg Ser
            370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Ser Lys Trp Met Phe Val Gly Arg Asn Lys Ala Gly
            435                 440                 445

Gln Val Trp Ser Asp Ile Thr Gly Asn Arg Thr Gly Val Thr Ile
450                 455                 460

Asn Ala Asp Gly Trp Ala Asn Phe Ser Val Asn Gly Gly Ser Val Ser
465                 470                 475                 480

Ile Trp Val Asn Lys
            485

<210> SEQ ID NO 12
<211> LENGTH: 480
<212> TYPE: PRT
<213> ORGANISM: Bacillus species

<400> SEQUENCE: 12

Asp Gly Leu Asn Gly Thr Met Met Gln Tyr Tyr Glu Trp His Leu Glu
1               5                   10                  15

Asn Asp Gly Gln His Trp Asn Arg Leu His Asp Asp Ala Ala Ala Leu
            20                  25                  30

Ser Asp Ala Gly Ile Thr Ala Ile Trp Ile Pro Pro Ala Tyr Lys Gly
        35                  40                  45

Asn Ser Gln Ala Asp Val Gly Tyr Gly Ala Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Ala Gln Leu Glu Arg Ala Ile Gly Ser Leu Lys Ser Asn Asp Ile Asn
                85                  90                  95

Val Tyr Gly Asp Val Val Met Asn His Lys Met Gly Ala Asp Phe Thr
            100                 105                 110

Glu Ala Val Gln Ala Val Gln Val Asn Pro Thr Asn Arg Trp Gln Asp
        115                 120                 125

Ile Ser Gly Ala Tyr Thr Ile Asp Ala Trp Thr Gly Phe Asp Phe Ser
    130                 135                 140

Gly Arg Asn Asn Ala Tyr Ser Asp Phe Lys Trp Arg Trp Phe His Phe
145                 150                 155                 160

Asn Gly Val Asp Trp Asp Gln Arg Tyr Gln Glu Asn His Ile Phe Arg
                165                 170                 175

Phe Ala Asn Thr Asn Trp Asn Trp Arg Val Asp Glu Glu Asn Gly Asn
            180                 185                 190

Tyr Asp Tyr Leu Leu Gly Ser Asn Ile Asp Phe Ser His Pro Glu Val
        195                 200                 205

Gln Asp Glu Leu Lys Asp Trp Gly Ser Trp Phe Thr Asp Glu Leu Asp
    210                 215                 220

Leu Asp Gly Tyr Arg Leu Asp Ala Ile Lys His Ile Pro Phe Trp Tyr
225                 230                 235                 240

Thr Ser Asp Trp Val Arg His Gln Arg Asn Glu Ala Asp Gln Asp Leu
```

```
                245                 250                 255
Phe Val Val Gly Glu Tyr Trp Lys Asp Asp Val Gly Ala Leu Glu Phe
                260                 265                 270

Tyr Leu Asp Glu Met Asn Trp Glu Met Ser Leu Phe Asp Val Pro Leu
                275                 280                 285

Asn Tyr Asn Phe Tyr Arg Ala Ser Gln Gln Gly Ser Tyr Asp Met
    290                 295                 300

Arg Asn Ile Leu Arg Gly Ser Leu Val Glu Ala His Pro Met His Ala
305                 310                 315                 320

Val Thr Phe Val Asp Asn His Asp Thr Gln Pro Gly Glu Ser Leu Glu
                325                 330                 335

Ser Trp Val Ala Asp Trp Phe Lys Pro Leu Ala Tyr Ala Thr Ile Leu
                340                 345                 350

Thr Arg Glu Gly Gly Tyr Pro Asn Val Phe Tyr Gly Asp Tyr Tyr Gly
                355                 360                 365

Ile Pro Asn Asp Asn Ile Ser Ala Lys Lys Asp Met Ile Asp Glu Leu
370                 375                 380

Leu Asp Ala Arg Gln Asn Tyr Ala Tyr Gly Thr Gln His Asp Tyr Phe
385                 390                 395                 400

Asp His Trp Asp Val Val Gly Trp Thr Arg Glu Gly Ser Ser Arg
                405                 410                 415

Pro Asn Ser Gly Leu Ala Thr Ile Met Ser Asn Gly Pro Gly Gly Ser
                420                 425                 430

Lys Trp Met Tyr Val Gly Arg Gln Asn Ala Gly Gln Thr Trp Thr Asp
                435                 440                 445

Leu Thr Gly Asn Asn Gly Ala Ser Val Thr Ile Asn Gly Asp Gly Trp
    450                 455                 460

Gly Glu Phe Phe Thr Asn Gly Gly Ser Val Ser Val Tyr Val Asn Gln
465                 470                 475                 480
```

<210> SEQ ID NO 13
<211> LENGTH: 483
<212> TYPE: PRT
<213> ORGANISM: Bacillus licheniformis

<400> SEQUENCE: 13

```
Ala Asn Leu Asn Gly Thr Leu Met Gln Tyr Phe Glu Trp Tyr Met Pro
1               5                   10                  15

Asn Asp Gly Gln His Trp Lys Arg Leu Gln Asn Asp Ser Ala Tyr Leu
                20                  25                  30

Ala Glu His Gly Ile Thr Ala Val Trp Ile Pro Pro Ala Tyr Lys Gly
            35                  40                  45

Thr Ser Gln Ala Asp Val Gly Tyr Gly Ala Tyr Asp Leu Tyr Asp Leu
        50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu Tyr Leu Ile Lys Ala Trp Thr His Phe His Phe Pro
    130                 135                 140
```

```
Gly Arg Gly Ser Thr Tyr Ser Asp Phe Lys Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Tyr Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Val Ala Glu Ile Lys Arg Trp Gly Thr Trp Tyr Ala Asn Glu Leu Gln
    210                 215                 220

Leu Asp Gly Asn Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe Tyr Ala Ala Ser Thr Gln Gly Gly Gly Tyr Asp Met
    290                 295                 300

Arg Lys Leu Leu Asn Asp Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp Tyr Asp Ile Thr Gly Asn Arg Ser Glu Pro Val Val Ile Asn Ser
    450                 455                 460

Glu Gly Trp Gly Glu Phe His Val Asn Asp Gly Ser Val Ser Ile Tyr
465                 470                 475                 480

Val Gln Arg

<210> SEQ ID NO 14
<211> LENGTH: 481
<212> TYPE: PRT
<213> ORGANISM: Artificial sequence
<220> FEATURE:
<223> OTHER INFORMATION: Synthetic construct

<400> SEQUENCE: 14

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
```

-continued

```
            20                  25                  30
Ile Gly Ile Thr Ala Val Trp Ile Pro Pro Ala Tyr Lys Ala Ile Ser
            35                  40                  45
Gln Ala Asp Val Gly Tyr Gly Ala Tyr Asp Leu Tyr Asp Leu Gly Glu
 50                  55                  60
Phe His Gln Lys Gly Thr Val Arg Thr Lys Tyr Gly Thr Lys Gly Glu
 65                  70                  75                  80
Leu Gln Ser Ala Ile Lys Ser Leu His Ser Arg Asp Ile Asn Val Tyr
            85                  90                  95
Gly Asp Val Val Ile Asn His Lys Ala Gly Ala Asp Ala Thr Glu Asp
            100                 105                 110
Val Thr Ala Val Glu Val Asp Pro Ala Asp Arg Asn Arg Val Ile Ser
            115                 120                 125
Gly Glu His Leu Ile Lys Ala Trp Thr His Phe His Phe Pro Gly Arg
            130                 135                 140
Gly Ser Thr Tyr Ser Asp Phe Lys Trp Tyr Trp Tyr His Phe Asp Gly
145                 150                 155                 160
Thr Asp Trp Asp Glu Ser Arg Lys Leu Asn Arg Ile Tyr Lys Phe Gln
                    165                 170                 175
Gly Lys Thr Trp Asp Trp Glu Val Ser Asn Glu Phe Gly Asn Tyr Asp
            180                 185                 190
Tyr Leu Met Tyr Ala Asp Phe Asp Tyr Asp His Pro Asp Val Val Ala
            195                 200                 205
Glu Ile Lys Arg Trp Gly Thr Trp Tyr Ala Asn Glu Leu Gln Leu Asp
            210                 215                 220
Gly Phe Arg Leu Asp Ala Val Lys His Ile Lys Phe Ser Phe Leu Arg
225                 230                 235                 240
Asp Trp Val Asn His Val Arg Glu Lys Thr Gly Lys Glu Met Phe Thr
                    245                 250                 255
Val Ala Glu Tyr Trp Ser Asn Asp Leu Gly Ala Leu Glu Asn Tyr Leu
            260                 265                 270
Asn Lys Thr Asn Phe Asn His Ser Val Phe Asp Val Pro Leu His Tyr
            275                 280                 285
Gln Phe His Ala Ala Ser Thr Gln Gly Gly Gly Tyr Asp Met Arg Lys
            290                 295                 300
Leu Leu Asn Gly Thr Val Val Ser Lys His Pro Leu Lys Ser Val Thr
305                 310                 315                 320
Phe Val Asp Asn His Asp Thr Gln Pro Gly Gln Ser Leu Glu Ser Thr
                    325                 330                 335
Val Gln Thr Trp Phe Lys Pro Leu Ala Tyr Ala Phe Ile Leu Thr Arg
            340                 345                 350
Glu Ser Gly Tyr Pro Gln Val Phe Tyr Gly Asp Met Tyr Gly Thr Lys
            355                 360                 365
Gly Asp Ser Gln Arg Glu Ile Pro Ala Leu Lys His Lys Ile Glu Pro
            370                 375                 380
Ile Leu Lys Ala Arg Lys Gln Tyr Ala Tyr Gly Ala Gln His Asp Tyr
385                 390                 395                 400
Phe Asp His His Asp Ile Val Gly Trp Thr Arg Glu Gly Asp Ser Ser
                    405                 410                 415
Val Ala Asn Ser Gly Leu Ala Ala Leu Ile Thr Asp Gly Pro Gly Gly
            420                 425                 430
Ala Lys Arg Met Tyr Val Gly Arg Gln Asn Ala Gly Glu Thr Trp His
            435                 440                 445
```

```
Asp Ile Thr Gly Asn Arg Ser Glu Pro Val Val Ile Asn Ser Glu Gly
    450                 455                 460

Trp Gly Glu Phe His Val Asn Gly Gly Ser Val Ser Ile Tyr Val Gln
465                 470                 475                 480

Arg
```

PROCESS FOR PREPARATION OF SUGARS AND SYRUPS

CROSS-REFERENCE TO RELATED APPLICATIONS

This application is a 35 U.S.C. 371 national application of PCT/US2014/033660 filed Apr. 10, 2015, which claims priority or the benefit under 35 U.S.C. 119 of U.S. provisional application No. 61/810,399 filed Apr. 10, 2013, the contents of which are fully incorporated herein by reference.

REFERENCE TO A SEQUENCE LISTING

This application contains a Sequence Listing in computer readable form, which is incorporated herein by reference.

FIELD OF THE INVENTION

The present invention relates to a process for the production of sugars and syrups, in particular high fructose corn syrup (HFCS).

BACKGROUND OF THE INVENTION

A large number of processes have been described for converting starch to starch hydrolysates, such as maltose, glucose or specialty syrups, either for use as sweeteners or as precursors for other saccharides such as fructose. Glucose may also be fermented to ethanol or other fermentation products.

Starch is a high molecular-weight polymer consisting of chains of glucose units. It usually consists of about 80% amylopectin and 20% amylose. Amylopectin is a branched polysaccharide in which linear chains of alpha-1,4 D-glucose residues are joined by alpha-1,6 glucosidic linkages.

Amylose is a linear polysaccharide built up of D-glucopyranose units linked together by alpha-1,4 glucosidic linkages. In the case of converting starch into a soluble starch hydrolysate, the starch is depolymerized. The conventional depolymerization process consists of a gelatinization step and two consecutive process steps, namely a liquefaction process and a saccharification process. Granular starch consists of microscopic granules, which are insoluble in water at room temperature. When an aqueous starch slurry is heated, the granules swell and eventually burst, dispersing the starch molecules into the solution. During this "gelatinization" process there is a dramatic increase in viscosity. As the solids level is 30-40% in a typical industrial process, the starch has to be thinned or "liquefied" so that it can be handled. This reduction in viscosity is today mostly obtained by enzymatic degradation.

HFCS is manufactured from high DX syrups, the term DX meaning percentage by weight of of dextrose (D-glucose) calculated on the basis of dry substance (DS) of syrup. The overall enzymatic process generally adopted for conversion of starch into high DX syrup is a two-stage process. The first step is the liquefaction, wherein the long-chained starch is degraded into smaller branched and linear units (maltodextrins) by an alpha-amylase. The liquefaction process is typically carried out at about 105-110° C. for about 5 to 10 minutes followed by about 1-2 hours at about 95° C. The temperature is then lowered to 60° C., a glucoamylase or a beta-amylase and optionally a debranching enzyme, such as an isoamylase or a pullulanase are added, and the saccharification process proceeds for about 24 to 72 hours.

WO 2013/057141 and WO 2013/057143 describe alpha-amylase variants and uses thereof in, e.g., starch processing, production of fermentation products, processes for producing fermentation products from ungelatinized starch-containing material, and processes for producing fermentation products from gelatinized starch-containing material. These variants are described as having, e.g., increased stability when incubated at low pH and/or at high temperature, in particular at low calcium concentrations, and in particular in the presence of at least 0.1% starch, e.g., in the presence of 0.9% or 1% starch.

There remains a need for improvement of processes for producing sugars and syrups.

SUMMARY OF THE INVENTION

In one aspect, the invention provides a process for producing a syrup:
a) liquefying an aqueous granular starch slurry with an alpha-amylase variant comprising an alteration at one or more positions corresponding to any of positions 1, 2, 68, 71, 126, 133, 142, 144, 156, 158, 176, 185, 201, 205, 213, 239, 279, 316, 318, 360, 416, 437 and 450 of SEQ ID NO: 1 to provide liquefied starch-containing material;
b) saccharifying the liquefied starch-containing material in the presence of a glucoamylase, and a pullulanase derived from *Bacillus deramificans Bacillus subtilis, Bacillus amyloderamificans,* or *Bacillus acidopullulyticus* to provide a dextrose syrup, and optionally
c) isomerizing to provide a fructose syrup.

In some aspects, the combination of the alpha-amylase variant, the glucoamylase, and the pullulanase derived from *Bacillus deramificans* produces an enhanced effect on final syrup observed, in particular an increase in DX as compared with DX percentages obtained without the combined enzymes.

BRIEF DESCRIPTION OF THE FIGURES

FIG. 1 shows an alignment of alpha-amylases with the amino acid sequences of:
SEQ ID NO: 1 is a *Bacillus licheniformis* alpha-amylase.
SEQ ID NO: 2 is a *Bacillus stearothermophilus* alpha-amylase.
SEQ ID NO: 3 is the *Bacillus* alpha-amylase TS-23 described in J. Appl. Microbiology, 1997, 82: 325-334 (SWALL:q59222).
SEQ ID NO: 4 is *Bacillus flavothermus* alpha-amylase AMY1048 described in WO 2005/001064.
SEQ ID NO: 5 is *Bacillus* alpha-amylase TS-22 described as SEQ ID NO: 21 in WO 04/113511.
SEQ ID NO: 6 is a *Bacillus amyloliquefaciens* alpha-amylase.
SEQ ID NO: 7 is *Bacillus* alkaline sp. SP690 amylase described as SEQ ID NO 1 in WO 95/26397.
SEQ ID NO: 8 is *Bacillus halmapalus* alpha-amylase described as SEQ ID NO 2 in WO 95/26397.
SEQ ID NO: 9 is *Bacillus* alkaline sp. AA560 amylase described as SEQ ID NO 4 in WO 00/60060.
SEQ ID NO: 10 is *Bacillus* alkaline sp. A 7-7 amylase described as SEQ ID NO 2 in WO 200210356.
SEQ ID NO: 11 is *Bacillus* alkaline sp. SP707 amylase described in Tsukamoto et al., 1988, Biochem. Biophys. Res. Commun. 151: 25-33).
SEQ ID NO: 12 is *Bacillus* alkaline sp. K-38 amylase described as SEQ ID NO 2 in EP 1022334.

SEQ ID NO: 13 is a *Bacillus licheniformis* alpha-amylase described in Lee et al, 2006, J. Biochem, 139: 997-1005.

SEQ ID NO: 14 is a variant alpha-amylase LE399 previously disclosed in, e.g., WO 2002/010355.

DETAILED DESCRIPTION OF THE INVENTION

Definitions

The term "granular starch" is understood as raw uncooked starch, i.e. starch that has not been subjected to a gelatinization. Starch is formed in plants as tiny granules insoluble in water. These granules are preserved in starches at temperatures below the initial gelatinization temperature. When put in cold water, the grains may absorb a small amount of the liquid. Up to 50° C. to 70° C. the swelling is reversible, the degree of reversibility being dependent upon the particular starch. With higher temperatures an irreversible swelling called gelatinization begins.

The term "Speciality Syrups", is an in the art recognised term and is characterised according to dextrose equivalent" (DE) and carbohydrate spectrum (See the article "New Speciality Glucose Syrups", p. 50+, in the textbook "Molecular Structure and Function of Food Carbohydrate", Edited by G. G. Birch and L. F. Green, Applied Science Publishers LTD., London). Typically Speciality Syrups have a DE in the range from 35 to 45.

Alpha-amylase: Alpha-amylases (E.C. 3.2.1.1) are a group of enzymes which catalyze the hydrolysis of starch and other linear and branched 1,4 glucosidic oligo- and polysaccharides. The skilled person will know how to determine alpha-amylase activity. It may be determined according to the procedure described in the Examples, e.g., by the PNP-G7 assay. In one aspect, the variants of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 1. In another aspect, a variant of the present application has at least 20%, e.g., at least 40%, at least 50%, at least 60%, at least 70%, at least 80%, at least 90%, at least 95%, or at least 100% of the alpha-amylase activity of its parent.

Glucoamylase: Glucoamylases are 1,4-alpha-D-glucan glucohydrolases (EC 3.2.1.3) that catalyze the release of D-glucose from the non-reducing ends of starch or related oligo- and polysaccharide molecules. For purposes of the present invention, glucoamylase activity is determined according to the procedure described in the "Materials and Methods"-section below. The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

Fragment: The term "fragment" means a polypeptide having one or more (e.g., several) amino acids absent from the amino and/or carboxyl terminus of a mature polypeptide; wherein the fragment has alpha-amylase activity. In one aspect, a fragment contains at least 300 amino acid residues, at least 350 amino acid residues, at least 400 amino acid residues, at least 450 amino acid residues, at least 470 amino acid residues, or at least 480 amino acid residues.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two or more different mature polypeptides (i.e., with a different C-terminal and/or N-terminal amino acid) expressed by the same polynucleotide. The mature form of some alpha-amylases, e.g., some bacterial alpha-amylases, comprises a catalytic domain containing the active site for substrate hydrolysis and one or more carbohydrate-binding modules (CBM) for binding to the carbohydrate substrate (starch) and optionally a polypeptide linking the CBM(s) with the catalytic domain, a region of the latter type usually being denoted a "linker".

Parent or parent alpha-amylase: The term "parent" or "parent alpha-amylase" means an alpha-amylase to which an alteration is made to produce the enzyme variants of the present invention. The parent may be a naturally occurring (wild-type) polypeptide or a variant or fragment thereof.

Pullulanase: Pullulanases (EC 3.2.1.41) hydrolyse alpha-1,6-D-glucosidic linkages in pullulan (a linear polymer of alpha-1,6-linked maltotriose units) and in amylopectin and glycogen, and the alpha- and beta-limit dextrins of amylopectin and glycogen. Other name(s) of pullulanase are e.g amylopullulanase, amylopectin 6-glucanohydrolase; bacterial debranching enzyme; debranching enzyme; alpha-dextrin endo-1,6-alpha-glucosidase; R-enzyme. The systematic name is "pullulan alpha-1,6-glucanohydrolase". Enzymes belonging to this class may comprise a carbohydrate binding module (CBM).

Carbohydrate binding module: Carbohydrate binding modules or carbohydrate binding domains are protein structures capable of binding a carbohydrate, usually with non-covalent bindings. Carbohydrate binding domains include domains binding polysaccharides such as cellulose, xylan or starch. Several carbohydrate binding domains have been described in the literature, and have been grouped in families, for review see Boraston et al. (2004) Biochem. J. 382: 769-781 and http://afmb.cnrs-mrs.fr/CAZY/index.html for the grouping of CBM families. A "starch binding domain" is a carbohydrate binding domain having specificity for starch, in particular raw starch. Starch binding domains are found in at least the carbohydrate binding domain families CBM-20, CBM-21, CBM-25, CBM-26, CBM-34, CBM-41 and CBM-45.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

Variant: The term "variant" means a polypeptide having alpha-amylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding one or more (e.g., several) amino acids, e.g., 1-5 amino acids, adjacent to the amino acid occupying a position. In one aspect, the variants of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 1. In another aspect, a variant of the present application has at least 20%, e.g., at least 40%, at least 50%, at least 60%, at least 70%, at least 80%, at least 90%, at least 95%, or at least 100% of the alpha-amylase activity of its parent. The alpha-amylase activity may be determined by the PNP-G7 assay described in the Examples.

Wild-type alpha-amylase: The term "wild-type" alpha-amylase means an alpha-amylase expressed by a naturally occurring microorganism, such as a bacterium, yeast, or filamentous fungus found in nature.

Conventions for Designation of Variants: For purposes of the present invention, the mature polypeptide disclosed in SEQ ID NO: 1 is used to determine the corresponding amino acid residue in another alpha-amylase. The amino acid sequence of another alpha-amylase is aligned with the mature polypeptide disclosed in SEQ ID NO: 1, and based on the alignment, the amino acid position number corresponding to any amino acid residue in the mature polypeptide disclosed in SEQ ID NO: 1 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another alpha-amylase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 1 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively. In the Examples of the present application, multiple mutations are separated by a space, e.g., G205R S411F representing G205R+S411F.

Deletions.

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G - K - A |

Multiple Alterations.

Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different Alterations.

Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:

"Tyr167Gly+Arg170Gly", "Tyr167Gly+Arg170Ala", "Tyr167Ala+Arg170Gly", and "Tyr167Ala+Arg170Ala".

Processes for Preparation of Sugars and Syrups

As disclosed in, e.g., WO 2013/057141 and WO 2013/057143, incorporated by reference herein, alpha-amylase variants comprising an alteration at one or more positions corresponding to any of positions 1, 2, 68, 71, 126, 133, 142, 144, 156, 158, 176, 185, 201, 205, 213, 239, 279, 316, 318, 360, 416, 437 and 450 of SEQ ID NO: 1 substitution show increased stability when incubated at low pH and/or at high temperature, in particular at low calcium concentrations, and in particular in the presence of at least 0.1% starch, e.g., in the presence of 0.9% or 1% starch.

The granular starch to be processed in the processes of the invention may in particular be obtained from tubers, roots, stems, legumes, cereals or whole grain. More specifically the granular starch may be obtained from corns, cobs, wheat, barley, rye, milo, sago, cassava, tapioca, sorghum, rice, peas, bean, banana or potatoes. Specially contemplated are both waxy and non-waxy types of corn and barley. The granular starch to be processed may be a highly refined starch quality, preferably more than 90%, 95%, 97% or 99.5% pure or it may be a more crude starch containing material comprising milled whole grain including non-starch fractions such as germ residues and fibres. The raw material, such as whole grain, is milled in order to open up the structure and allowing for further processing. Two milling processes are preferred according to the invention: wet and dry milling. In dry milling the whole kernel is milled and used. Wet milling gives a good separation of germ and meal (starch granules and protein) and is with a few exceptions applied at locations where the starch hydrolysate is used in production of syrups. Both dry and wet milling are well known in the art of starch processing and are equally contemplated for the processes of the invention. The processes of the invention may be conducted in an ultrafiltration system where the retentate is held under recirculation in presence of enzymes, raw starch and water and where the permeate is the soluble starch hydrolysate. Equally contemplated is the process conducted in a continuous membrane reactor with ultrafiltration membranes and where the retentate is held under recirculation in presence of enzymes, raw starch and water and where the permeate is the soluble starch hydrolysate. Also contemplated is the process conducted in a continuous membrane reactor with microfiltration membranes and where the retentate is held under recirculation in presence of enzymes, raw starch and water and where the permeate is the soluble starch hydrolysate.

The starch slurry to be subjected to the processes of the invention may have 20-55% dry solids granular starch, preferably 25-40% dry solids granular starch, more preferably 30-35% dry solids granular starch.

After being subjected to the processes of the invention at least 85%, 86%, 87%, 88%, 89%, 90%, 91%, 92%, 93%, 94%, 95%, 96%, 97%, 98%, or preferably 99%, in particular at least 99.1%, 99.2%, 99.3%, 99.4%, 99.5%, 99.6%, 99.7%, 99.8%, or 99.9% of the dry solids of the granular starch is converted into a syrup, e.g., a dextrose syrup or glucose syrup.

Analyses of dextrose syrup and processes for its further purification and/or concentration are well known in the art.

In some aspects, the combination of the alpha-amylase variant, the glucoamylase, and the pullulanase derived from *Bacillus deramificans* produces an enhanced effect on final syrup observed, in particular an increase in DX as compared with DX percentages obtained without the combined enzymes.

In some aspects, alpha-amylase variant may be added during the saccharification step b).

Addition of the alpha-amylase variant in liquefaction step a), saccharification step b), or a combination thereof can result in improvements compared to a similar reaction without the alpha-amylase variant. Improvements may include, for example, higher DP1 product, reduced DP4+ product, and/or reduced DP2 product compared to a similar reaction without the alpha-amylase variant.

Liquefaction Process

"Liquefaction" is a process in which the long-chained starch is degraded into branched and linear shorter units (maltodextrins) by an alpha-amylase. Liquefaction may be carried out as a three-step hot slurry process. The slurry is heated to between 60-95° C. (e.g., 70-90° C.) and an alpha-amylase is added to initiate liquefaction (thinning).

The slurry may in an embodiment be jet-cooked at between 95-140° C., e.g., 105-125° C., for about 1-15 minutes, e.g., about 3-10 minutes, especially around 5 minutes. The slurry is then cooled to 60-95° C. and more alpha-amylase is added to obtain final hydrolysis (secondary liquefaction). The jet-cooking process is carried out at pH 4.5-6.5, typically at a pH between 5 and 6. The alpha-amylase may be added as a single dose, e.g., before jet cooking.

The liquefaction process is carried out at between 70-95° C., such as 80-90° C., such as around 85° C., alternatively around 95° C., for about 10 minutes to 5 hours, typically for 1-2 hours. The pH is between 4 and 7, such as between 5.5 and 6.2. In order to ensure optimal enzyme stability under these conditions, calcium may optionally be added (to provide 1-60 ppm free calcium ions, such as about 40 ppm free calcium ions). After such treatment, the liquefied starch will typically have a "dextrose equivalent" (DE) of 4-40, such as 4-28, including 8-15, such as 9-13, including 9-12, or even 10-15. According to a preferred embodiment, liquefaction is carried out by jet-cooking at a temperature in the range of 100-115° C. for 1-60 minutes, cooling to 90-100° C. and holding for 30-120 minutes at a pH of about 5.5-6.0.

Generally liquefaction and liquefaction conditions are well known in the art.

Saccharification Process

"Saccharification" is a process in which maltodextrins (such as liquefied starch-containing material) is converted to low molecular sugars, such as DP1-3 sugars. Saccharification of liquefied starch-containing material is well known in the art. Standard saccharification is typically performed enzymatically using at least one carbohydrate-source generating enzyme, such as especially glucoamylase.

According to the present invention liquefied starch-containing material is saccharified in the presence of, e.g., a glucoamylase and a pullulanase derived from *Bacillus deramificans, Bacillus subtilis, Bacillus amyloderamificans*, or *Bacillus acidopullulyticus*. As for standard saccharification processes, a saccharification process of the invention may last up to from 20 to 100 hours, preferably about 24 to about 72 hours, such as about 30 to about 60 hours, and may preferably be carried out at a temperature in the range from about 30 to 65° C., more preferably about 60° C., and at a pH between 4 and 6, normally around pH 4.5-5.5, or around pH 4.0-4.5.

Isomerization Process

In some embodiments, the dextrose syrup is subjected to conversion into fructose syrup, such as high fructose starch-based syrup (HFSS), such as high fructose corn syrup (HFCS). This conversion is preferably achieved using a glucose isomerase, and more preferably by an immobilized glucose isomerase supported on a solid support. Contemplated isomerases comprises the commercial products Sweetzyme™ IT from Novozymes NS, G-zyme™ IMGI and G-zyme™ G993, Ketomax™ and G-zyme™ G993 from Rhodia, G-zyme™ G993 liquid and GenSweet™ IGI from Genencor Int.

Alpha-amylase Variants

An alpha-amylase variant useful according to the invention is described, e.g., in WO 2013/057141 and WO 2013/057143, incorporated by reference herein.

In particular, alpha-amylase variants comprising an alteration at one or more positions corresponding to any of positions 1, 2, 68, 71, 126, 133, 142, 144, 156, 158, 176, 185, 201, 205, 213, 239, 279, 316, 318, 360, 416, 437 and 450 of SEQ ID NO: 1, wherein the variant has at least 60% and less than 100% sequence identity to (i) the mature polypeptide of any of SEQ ID NOs: 1, 2, 3, 4, 5, 6, 7, 8, 9, 10, 11, 12, 13 or 14, or (ii) amino acids 1 to 483 of SEQ ID NO: 1, amino acids 1 to 483 of SEQ ID NO: 2, amino acids 1 to 485 of SEQ ID NO: 3, amino acids 1 to 482 of SEQ ID NO: 4, amino acids 1 to 484 of SEQ ID NO: 5, amino acids 1 to 483 of SEQ ID NO: 6, amino acids 1 to 485 of SEQ ID NO: 7, amino acids 1 to 485 of SEQ ID NO: 8, amino acids 1 to 485 of SEQ ID NO: 9, amino acids 1 to 485 of SEQ ID NO: 10, amino acids 1 to 485 of SEQ ID NO: 11, amino acids 1 to 480 of SEQ ID NO: 12, amino acids 1 to 483 of SEQ ID NO: 13 or amino acids 1 to 481 of SEQ ID NO: 14, and wherein the variant has alpha-amylase activity.

Preferably, the variants are isolated.

Alpha-amylase variants contemplated herein preferably comprise a substitution at one or more positions corresponding to any of positions 1, 2, 68, 71, 126, 133, 142, 144, 156, 158, 176, 185, 201, 205, 213, 239, 279, 316, 318, 360, 416, 437 and 450 of SEQ ID NO: 1, wherein the variant has at least 60% and less than 100% sequence identity to (i) the mature polypeptide of any of SEQ ID NOs: 1, 2, 3, 4, 5, 6, 7, 8, 9, 10, 11, 12, 13 or 14, or (ii) amino acids 1 to 483 of SEQ ID NO: 1, amino acids 1 to 483 of SEQ ID NO: 2, amino acids 1 to 485 of SEQ ID NO: 3, amino acids 1 to 482 of SEQ ID NO: 4, amino acids 1 to 484 of SEQ ID NO: 5, amino acids 1 to 483 of SEQ ID NO: 6, amino acids 1 to 485 of SEQ ID NO: 7, amino acids 1 to 485 of SEQ ID NO: 8, amino acids 1 to 485 of SEQ ID NO: 9, amino acids 1 to 485 of SEQ ID NO: 10, amino acids 1 to 485 of SEQ ID NO: 11, amino acids 1 to 480 of SEQ ID NO: 12, amino acids 1 to 483 of SEQ ID NO: 13 or amino acids 1 to 481 of SEQ ID NO: 14, and wherein the variant has alpha-amylase activity.

In one embodiment, the variant comprises one or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, K176L, E185P, I201F, I201Y, H205Y, K213T, S239A, S239Q, F279Y, F279W, H316F, H316Y, H316W, L318F, L318H, L318Y, L318W, Q360S, D416V, R437F, R437H, R437Y, R437W, H450F, H450Y and H450W.

In a preferred embodiment, the variant comprises one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

In another preferred embodiment, the variant comprises two or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

In another embodiment, the variant comprises three or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W. In another embodiment, the variant comprises four or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

In one embodiment, the variant comprises a substitution at a position corresponding to position 176, in particular the substitution K176L, in combination with an alteration at one or more positions corresponding to any of positions 1, 2, 68, 71, 126, 133, 142, 144, 156, 158, 185, 201, 205, 213, 239, 279, 316, 318, 360, 416, 437 and 450, in particular one or more alterations selected from the group consisting of A1AH, A1AW, A1H, A1W, N2NH, N2NW, N2H, N2W, H68W, G71W, N126W, H133Y, H142W, P144W, Y156W, Y158W, E185P, I201Y, H205Y, K213T, S239A, S239Q, F279W, H316W, L318W, Q360S, D416V, R437W and H450W.

In a preferred embodiment, the variant comprises a substitution at a position corresponding to position 176, in particular the substitution K176L, in combination with an alteration at one or more positions corresponding to any of positions 1, 2, 68, 71, 126, 133, 142, 144, 156, 158, 185, 201, 205, 213, 239, 279, 316, 318, 360, 416, 437 and 450, in particular one or more alterations selected from the group consisting of A1AH, A1AW, A1H, A1W, N2NH, N2NW, N2H, N2W, H68W, G71W, N126W, H133Y, H142W, P144W, Y156W, Y158W, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 176, in particular the substitution K176L, in combination with an alteration at one or more positions corresponding to any of positions 1, 2, 68, 71, 126, 133, 142, 144, 156, 158, 185, 201, 205, 213, 239, 279, 316, 318, 360, 416, 437 and 450, in particular one or more alterations selected from the group consisting of A1AH, A1AW, A1H, A1W, N2NH, N2NW, N2H, N2W, H68W, G71W, N126W, H133Y, H142W, P144W, Y156W, Y158W, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 185, in particular the substitution E185P, in combination with a substitution at one or more positions corresponding to any of positions 1, 2, 68, 71, 126, 133, 142, 144, 156, 158, 176, 201, 205, 213, 239, 279, 316, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, I201Y, H205Y, K213T, S239A, S239Q, F279W, H316W, L318W, Q360S, D416V, R437W and H450W.

In a preferred embodiment, the variant comprises a substitution at a position corresponding to position 185, in particular the substitution E185P, in combination with a substitution at one or more positions corresponding to any of positions 1, 2, 68, 71, 126, 133, 142, 144, 156, 158, 176, 201, 205, 213, 239, 279, 316, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 185, in particular the substitution E185P, in combination with a substitution at one or more positions corresponding to any of positions 1, 2, 68, 71, 126, 133, 142, 144, 156, 158, 176, 201, 205, 213, 239, 279, 316, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 360, in particular the substitution Q360S, in combination with a substitution at one or more positions corresponding to any of positions 1, 2, 68, 71, 126, 133, 142, 144, 156, 158, 176, 185, 201, 205, 213, 239, 279, 316, 318, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, D416V, R437W and H450W.

In a preferred embodiment, the variant comprises a substitution at a position corresponding to position 360, in particular the substitution Q360S, in combination with a substitution at one or more positions corresponding to any of positions 1, 2, 68, 71, 126, 133, 142, 144, 156, 158, 176, 185, 201, 205, 213, 239, 279, 316, 318, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 360, in particular the substitution Q360S, in combination with a substitution at one or more positions corresponding to any of positions 1, 2, 68, 71, 126, 133, 142, 144, 156, 158, 176, 185, 201, 205, 213, 239, 279, 316, 318, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 437, in particular the substitution R437W, in combination with a substitution at one or more positions corresponding to any of positions 1, 2, 68, 71, 126, 133, 142, 144, 156, 158, 176, 185, 201, 205, 213, 239, 279, 316, 318, 360, 416 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V and H450W.

In a preferred embodiment, the variant comprises a substitution at a position corresponding to position 437, in particular the substitution R437W, in combination with a substitution at one or more positions corresponding to any of positions 1, 2, 68, 71, 126, 133, 142, 144, 156, 158, 176, 185, 201, 205, 213, 239, 279, 316, 318, 360, 416 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 437, in particular the substitution R437W, in combination with a substitution at one or more positions corresponding to any of positions 1, 2, 68, 71, 126, 133, 142, 144, 156, 158, 176, 185, 201, 205, 213, 239, 279, 316, 318, 360, 416 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In a preferred embodiment, a variant comprises a set of substitutions selected from the group consisting of:
A1H+N2W+K176L+E185P,
A1W+N2H+K176L+E185P,
N2H+H68W+H133Y+K176L+E185P,
N2H+H68W+Y156W+K176L+E185P,
N2H+H68W+Y158W+K176L+E185P,
N2H+H68W+K176L+E185P,
N2H+H68W+K176L+E185P+I201Y+H205Y+D207V+V209D,
N2H+H68W+K176L+E185P+F279W,
N2H+H133Y+K176L+E185P+H316W+R437W,
N2H+H133Y+K176L+E185P+Q360S+R437W,
N2H+H142W+K176L+E185P+H316W+R437W,
N2H+H142W+K176L+E185P+Q360S+R437W,
N2H+P144W+K176L+E185P,
N2H+Y156W+Y158W+K176L+E185P+H316W+R437W,
N2H+Y156W+K176L+E185P+Q360S+R437W,
N2H+Y158W+K176L+E185P+I201Y+H205Y+D207V+V209D+H316W,
N2H+K176L+E185P,
N2H+K176L+E185P+H316W,
N2H+K176L+E185P+H316W+L318W+R437W,
N2H+K176L+E185P+H316W+Q360S+R437W,
N2H+K176L+E185P+H316W+R437W,
N2H+K176L+E185P+R437W,
N2H+K176L+E185P+Q360S+R437W,
N2H+K176L+E185P+H316W+Q360S+R437W,
N2H+K176L+I201Y+H205Y+K213T+Q360S+D416V+R437W,
H68W+K176L+E185P,
H68W+K176L+E185P+I201Y+H205Y+K213T+Q360S+D416V+R437W,
H68W+K176L+I201Y+H205Y+K213T+Q360S+D416V+R437W,
G71W+K176L+E185P,
N126W+K176L+I201Y+H205Y+K213T+Q360S+D416V+R437W,
H133Y+Y158W+K176L+E185P+I201Y+H205Y+K213T+Q360S+D416V+R437W,
H133Y+K176L+I201Y+H205Y+K213T+Q360S+D416V+R437W,
H142W+Y158W+K176L+E185P+I201Y+H205Y+K213T+Q360S+D416V+R437W,
H142W+K176L+E185P,
H142W+K176L+E185P+I201Y+H205Y+K213T+Q360S+D416V+R437W,
H142W+K176L+I201Y+H205Y+K213T+Q360S+D416V+R437W,
P144W+K176L+E185P,
Y156W+Y158W+K176L+E185P+I201Y+H205Y+K213T+Q360S+D416V+R437W,
Y156W+Y158W+K176L+E185P+H316W+R437W,
Y156W+K176L+E185P+Q360S+R437W,
Y156W+K176L+I201Y+H205Y+K213T+Q360S+D416V+R437W,
Y158W+K176L+E185P,
Y158W+K176L+E185P+I201Y+H205Y+D207V+V209D+H316W,
Y158W+K176L+E185P+I201Y+H205Y+K213T+H316L+L318W+Q360S+D416V+R437,
Y158W+K176L+E185P+I201Y+H205Y+K213T+H316W+Q360S+D416V+R437W,
Y158W+K176L+E185P+I201Y+H205Y+K213T+Q360S+D416V+R437W,
Y158W+K176L+I201Y+H205Y+K213T+Q360S+D416V+R437W,
K176L+E185P,
K176L+E185P+I201Y+H205Y+K213T+Q360S+D416V+R437W,
K176L+E185P+I201Y+H205Y+R437W,
K176L+E185P+F279W,
K176L+E185P+H316W,
K176L+E185P+L318W,
K176L+E185P+H450W,
K176L+I201Y+H205Y+K213T+S239Q+Q360S+D416V+R437W,
K176L+I201Y+H205Y+K213T+H316W+Q360S+D416V+R437W,
K176L+I201Y+H205Y+K213T+L318W+Q360S+D416V+R437W,
K176L+I201Y+H205Y+K213T+Q360S+D416V+R437W,
K176L+I201Y+H205Y+K213T+Q360S+R437W,
K176L+I201Y+H205Y+K213T+D416V+R437W, and
K176L+I201Y+H205Y+Q360S+D416V+R437W.

In another preferred embodiment, the variant comprises a set of substitutions selected from the group consisting of:
A1H+N2W+K176L+E185P,
A1W+N2H+K176L+E185P,
N2H+H68W+H133Y+K176L+E185P,
N2H+H68W+Y156W+K176L+E185P,
N2H+H68W+Y158W+K176L+E185P,
N2H+H68W+K176L+E185P,
N2H+H68W+K176L+E185P+I201Y+H205Y+D207V+V209D,
N2H+H68W+K176L+E185P+F279W,
N2H+H133Y+K176L+E185P+H316W+R437W,
N2H+H133Y+K176L+E185P+Q360S+R437W,
N2H+H142W+K176L+E185P+H316W+R437W,
N2H+H142W+K176L+E185P+Q360S+R437W,
N2H+P144W+K176L+E185P,
N2H+Y156W+Y158W+K176L+E185P+H316W+R437W,
N2H+Y156W+K176L+E185P+Q360S+R437W,
N2H+Y158W+K176L+E185P+I201Y+H205Y+D207V+V209D+H316W, N2H+K176L+E185P,
N2H+K176L+E185P+H316W,
N2H+K176L+E185P+H316W+L318W+R437W,
N2H+K176L+E185P+H316W+Q360S+R437W,
N2H+K176L+E185P+H316W+R437W,
N2H+K176L+E185P+R437W,
N2H+K176L+E185P+Q360S+R437W,
N2H+K176L+E185P+H316W+Q360S+R437W,
N2H+K176L+I201Y+H205Y+K213T+Q360S+D416V+
R437W,
H68W+K176L+E185P,
H68W+K176L+E185P+I201Y+H205Y+K213T+Q360S+
D416V+R437W,
H68W+K176L+I201Y+H205Y+K213T+Q360S+D416V+
R437W,
G71W+K176L+E185P,
N126W+K176L+I201Y+H205Y+K213T+Q360S+D416V+
R437W,
H133Y+Y158W+K176L+E185P+I201Y+H205Y+K213T+
Q360S+D416V+R437W,
H133Y+K176L+I201Y+H205Y+K213T+Q360S+D416V+
R437W,
H142W+Y158W+K176L+E185P+I201Y+H205Y+
K213T+Q360S+D416V+R437W,
H142W+K176L+E185P,
H142W+K176L+E185P+I201Y+H205Y+K213T+Q360S+
D416V+R437W,
H142W+K176L+I201Y+H205Y+K213T+Q360S+D416V+
R437W,
P144W+K176L+E185P,
Y156W+Y158W+K176L+E185P+I201Y+H205Y+
K213T+Q360S+D416V+R437W,
Y156W+Y158W+K176L+E185P+H316W+R437W,
Y156W+K176L+E185P+Q360S+R437W,
Y156W+K176L+I201Y+H205Y+K213T+Q360S+D416V+
R437W,
Y158W+K176L+E185P,
Y158W+K176L+E185P+I201Y+H205Y+D207V+V209D+
H316W,
Y158W+K176L+E185P+I201Y+H205Y+K213T+H316L+
L318W+Q360S+D416V+R437W,
Y158W+K176L+E185P+I201Y+H205Y+K213T+
H316W+Q360S+D416V+R437W,
Y158W+K176L+E185P+I201Y+H205Y+K213T+Q360S+
D416V+R437W,
Y158W+K176L+I201Y+H205Y+K213T+Q360S+D416V+
R437W,
K176L+E185P,
K176L+E185P+I201Y+H205Y+K213T+Q360S+D416V+
R437W,
K176L+E185P+I201Y+H205Y+R437W,
K176L+E185P+F279W,
K176L+E185P+H316W,
K176L+E185P+L318W,
K176L+E185P+H450W,
K176L+I201Y+H205Y+K213T+S239Q+Q360S+D416V+
R437W,
K176L+I201Y+H205Y+K213T+H316W+Q360S+D416V+
R437W,
K176L+I201Y+H205Y+K213T+L318W+Q360S+D416V+
R437W,
K176L+I201Y+H205Y+K213T+Q360S+D416V+R437W,
K176L+I201Y+H205Y+K213T+Q360S+R437W,
K176L+I201Y+H205Y+K213T+D416V+R437W, and
K176L+I201Y+H205Y+Q360S+D416V+R437W.

In a preferred embodiment, the variant comprises a set of substitutions selected from the group consisting of:
T49H+K176L+E185P,
T49G+K176L+E185P,
T49L+S50T+K176L+E185P,
T116G+K176L+E185P,
K176L+E185P,
K176L+E185P+I201Y+H205Y+K213T+Q360S+D416V+
R437W,
K176L+E185P+L241D,
K176L+E185P+R375V, and
K176L+E185P+R375G.

In another preferred embodiment, the variant comprises a set of substitutions selected from the group consisting of:
G48A+T49H+G107A+H156Y+K176L+A181T+E185P+
N190F+I201F+A209V+Q264S;
G48A+T49G+G107A+H156Y+K176L+A181T+E185P+
N190F+I201F+A209V+Q264S;
G48A+T49L+S50T+G107A+H156Y+K176L+A181T+
E185P+N190F+I201F+A209V+Q264S;
G48A+T49I+G107A+T116G+H156Y+K176L+A181T+
E185P+N190F+I201F+A209V+Q264S;
G48A+T49I+G107A+H156Y+K176L+A181T+E185P+
N190F+I201F+A209V+Q264S;
G48A+T49I+G107A+H156Y+K176L+A181T+E185P+
N190F+I201Y+H205Y+A209V+K213T+Q264S+
Q360S+D416V+R437W;
G48A+T49I+G107A+H156Y+K176L+A181T+E185P+
N190F+I201F+L241D+A209V+Q264S;
G48A+T49I+G107A+H156Y+K176L+A181T+E185P+
N190F+I201F+A209V+Q264S+R375V;
G48A+T49I+G107A+H156Y+K176L+A181T+E185P+
N190F+I201F+A209V+Q264S+R375G; and
G48A+G107A+H156Y+K176L+A181T+E185P+N190F+
I201F+A209V+Q264S.

In one embodiment, the variant comprises a substitution at position 176 and/or 185. Preferably the substitution is 176+185, and more preferably K176L+E185P.

In one embodiment, the variant comprises a substitution at one or more of positions 176, 185, 360 and/or 437. Preferably the substitution is 176+185+360+437, more preferably K176L+E185P+Q360S+R437W.

In one embodiment, the variant further comprises a deletion at both of the two positions immediately before the position corresponding to position 180 of SEQ ID NO: 1. I.e., a deletion of the two amino acids corresponding to positions 181 and 182 of SEQ ID NO: 2.

In another embodiment, the variant further comprises a deletion of two amino acids after the position corresponding to position 177 of SEQ ID NO: 1 and before the position corresponding to position 180 of SEQ ID NO: 1. I.e., a deletion of two amino acids in the R179-G180-I181-G182 peptide of SEQ ID NO: 2, or homologous amino acids in any of SEQ ID NO: 3 to 11.

The variants may further comprise one or more (e.g., several) additional alterations, e.g., one or more (e.g., several) additional substitutions.

The additional amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for alpha-amylase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

The variants may consist of 300 to 700, e.g., 350 to 650, 400 to 600, 450 to 500 or 470 to 490, amino acids.

In a particular aspect, the alpha-amylase variant is present in an amount of about 0.0001-3 mg enzyme protein per gram dry solids, such as 0.0005-2 mg EP/g DS, preferably 0.001-1 mg/g DS, more preferably 0.005-0.5 mg EP/g DS, and even more preferably 0.005-0.006 mg EP/g.

Glucoamylase

In a preferred embodiment the glucoamylase (E.C.3.2.1.3) may be derived from a microorganism or a plant.

The glucoamylase is preferably one derived from a strain of the genus Aspergillus, preferably A. niger, A. awamori or A. oryzae, or a strain of Talaromyces, preferably a strain of Talaromyes emersonii or a strain of Athelia, preferably Athelia rolfsii (previously denoted Corticium rolfsii—see, e.g., U.S. Pat. No. 4,727,026).

Preferred are Trametes glucoamylases, such as glucoamylase from Trametes cingulata (WO 2006/069289), or variants or fragments thereof.

Exemplary glucoamylase of fungal or bacterial origin selected from the group consisting of Aspergillus glucoamylases, in particular A. niger G1 or G2 glucoamylase (Boel et al., 1984, EMBO J. 3 (5): 1097-1102), or variants thereof, such as disclosed in WO 92/00381 and WO 00/04136; the A. awamori glucoamylase (WO 84/02921), A. oryzae (Agric. Biol. Chem., 1991, 55(4): 941-949), or variants or fragments thereof.

Other contemplated Aspergillus glucoamylase variants include variants to enhance the thermal stability: G137A and G139A (Chen et al., 1996, Prot. Engng. 9: 499-505); D257E and D293E/Q (Chen et al., 1995, Prot. Engng. 8: 575-582); N182 (Chen et al., 1994, Biochem. J. 301: 275-281); disulphide bonds, A246C (Fierobe et al., 1996, Biochemistry, 35: 8698-8704; and introduction of Pro residues in position A435 and S436 (Li et al., 1997, Protein Engng. 10: 1199-1204. Furthermore Clark Ford presented a paper on Oct. 17, 1997, ENZYME ENGINEERING 14, Beijing/China Oct. 12-17, 1997, Abstract book p. 0-61. The abstract suggests mutations in positions G137A, N20C/A27C, and S30P in an Aspergillus awamori glucoamylase to improve the thermal stability.

Other contemplated glucoamylases include Talaromyces glucoamylases, in particular derived from Talaromyces emersonii (WO 99/28448), Talaromyces leycettanus (U.S. Pat. No. RE 32,153), Talaromyces duponti, Talaromyces thermophilus (U.S. Pat. No. 4,587,215). Bacterial glucoamylases contemplated include glucoamylases from the genus Clostridium, in particular C. thermoamylolyticum (EP 135138), and C. thermohydrosulfuricum (WO 86/01831). Preferred glucoamylases include the glucoamylases derived from Aspergillus oryzae. Also contemplated are the commercial products AMG 200L; AMG 300L; SAN™ SUPER and AMG™ E (from Novozymes); OPTIDEX™ 300 (from Genencor Int.); AMIGASE™ and AMIGASE™ PLUS (from DSM); G-ZYME™ G900 (from Enzyme Bio-Systems); G-ZYME™ G990 ZR (A. niger glucoamylase and low protease content).

A glucoamylase may suitably be added in amounts of between 0.005-2 AGU/g DS, preferably 0.02-2.0 AGU/g DS, preferably 0.01-1 AGU/g DS, such as especially around 0.3 AGU/g DS, or around 0.2 AGU/g DS. Glucoamylases may also be added in other effective amounts well known to the person skilled in the art.

Pullulanase

Pullulanases (E.C. 3.2.1.41, pullulan 6-glucano-hydrolase), are debranching enzymes characterized by their ability to hydrolyze the alpha-1,6-glycosidic bonds in, for example, amylopectin and pullulan.

The pullulanase may be any pullulanase, preferably a bacterial pullulanase, preferably derived from a strain of the genus Bacillus, especially derived from a strain of Bacillus deramificans, Bacillus subtilis, Bacillus amyloderamificans, or Bacillus acidopullulyticus.

Specifically contemplated pullulanases useful according to the present invention include the pullulanases the Bacillus deramificans disclosed as Sequence Number 4 in WO 01/151620 (hereby incorporated by reference), as well as the pullulanases from Bacillus deramificans disclosed as Sequences 2, 4, and 6 of WO 2008/024372 (hereby incorporated by reference).

Specifically contemplated pullulanases useful according to the present invention include the pullulanases from Bacillus amyloderamificans disclosed in U.S. Pat. No. 4,560,651 (hereby incorporated by reference), the pullulanase disclosed as SEQ ID NO: 2 in WO 01/151620 (hereby incorporated by reference), and the pullulanase from Bacillus acidopullulyticus disclosed as SEQ ID NO: 6 in WO 01/151620 (hereby incorporated by reference) and also described in FEMS Mic. Let. (1994) 115, 97-106.

The pullulanase may according to the invention be added in an effective amount which include the preferred range of from between 1-100 micro g per g DS, especially from 10-60 micro g per g DS. Pullulanase activity may be determined as NPUN. An Assay for determination of NPUN is described in the "Materials & Methods"-section below.

In a preferred embodiment the pullulanase is used in an amount between 1-100 micro g enzyme protein per g DS, preferably between 10-60 micro g enzyme protein per g DS. Suitable commercially available pullulanase products include PROMOZYME D, PROMOZYME™ D2 (Novozymes NS, Denmark), OPTIMAX L-1000, OPTIMAX L-300, and AMANO 8 (Amano, Japan).

Blend having Glucoamylase and Pullulanase Activity

In a preferred embodiment, the saccharification is performed in the presence of an blend, such as a commercial product having a mixture of enzyme activity comprising at least glucoamylase and pullulanase activity. Other activities may also be present in the product. Exemplary blends having glucoamylase and pullulanase activity include DEXTROZYME DX 2.0× (Novozymes A/S, Denmark), DEXTROZYME DX H (Novozymes A/S, Denmark), DEXTROZYME DX 1.5× (Novozymes A/S, Denmark), DEXTROZYME DX PLUS 1.5× (Novozymes A/S, Denmark), SUHONG GA FERMENT, OPTIMAX 4060 VHP (Genencor Int., USA), OPTIMAX SUPRA (Genencor Int., USA).

Additional Enzymes

In some embodiments, the processes of the invention optionally comprise additional enzymes.

Fungal Alpha-Amylase

A particular enzyme to be used as additional enzyme in the processes of the invention is a fungal alpha-amylase (EC 3.2.1.1), such as a fungamyl-like alpha-amylase. In the present disclosure, the term "fungamyl-like alpha-amylase" indicates an alpha-amylase which exhibits a high homology, i.e. more than 50%, 55%, 60%, 65%, 70%, 75%, 80%, 85% or even 90% homology to the amino acid sequence of SEQ ID NO: 7. Fungal alpha-amylases may be added in an amount of 0.001-1.0 AFAU/g DS, preferably from 0.002-0.5 AFAU/g DS, preferably 0.02-0.1 AFAU/g DS, or in other effective amounts well known to the person skilled in the art.

Beta-Amylase

Another particular enzyme to be used as additional enzyme in the processes of the invention may be a beta-amylase (E.C 3.2.1.2). Beta-amylase is the name traditionally given to exo-acting maltogenic amylases, which catalyze the hydrolysis of 1,4-alpha-glucosidic linkages in amylose, amylopectin and related glucose polymers.

Beta-amylases have been isolated from various plants and microorganisms (W. M. Fogarty and C. T. Kelly, 1979, Progress in Industrial Microbiology, 15: 112-115). These beta-amylases are characterized by having optimum temperatures in the range from 40° C. to 65° C. and optimum pH in the range from 4.5 to 7.0. Contemplated beta-amylases include the beta-amylase from barley Spezyme® BBA 1500, Spezyme® DBA and Optimalt ME, Optimalt™ BBA from Genencor Int. as well as Novozym™ WBA from Novozymes NS. Beta-amylases can be added in effective amounts well known to the person skilled in the art.

Bacillus Alpha-Amylase

A Bacillus alpha-amylase (often referred to as "Termamyl-like alpha-amylases"). Well-known Termamyl-like alpha-amylases include alpha-amylase derived from a strain of B. licheniformis (commercially available as Termamyl), B. amyloliquefaciens, and B. stearothermophilus alpha-amylase. Other Termamyl-like alpha-amylases include alpha-amylase derived from a strain of the Bacillus sp. NCIB 12289, NCIB 12512, NCIB 12513 or DSM 9375, all of which are described in detail in WO 95/26397, and the alpha-amylase described by Tsukamoto et al., 1988, Biochemical and Biophysical Research Communications, 151: 25-31. In the context of the present invention a Termamyl-like alpha-amylase is an alpha-amylase as defined in WO 99/19467 on page 3, line 18 to page 6, line 27. Contemplated variants and hybrids are described in WO 96/23874, WO 97/41213, and WO 99/19467. Specifically contemplated is a recombinant B. stearothermophilus alpha-amylase variant with the mutations: I181*+G182*+N193F. Bacillus alpha-amylases may be added in effective amounts well known to the person skilled in the art.

Debranching Enzymes

Another particular enzyme of the process may be a debranching enzyme, such as an isoamylase (E.C. 3.2.1.68) or another pullulanase (E.C. 3.2.1.41). Isoamylase hydrolyses alpha-1,6-D-glucosidic branch linkages in amylopectin and beta-limit dextrins and can be distinguished from pullulanases by the inability of isoamylase to attack pullulan, and by the limited action on alpha-limit dextrins. Debranching enzyme may be added in effective amounts well known to the person skilled in the art.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Materials and Methods

Assays for Measurement of Amylolytic Activity (Alpha-Amylase Activity)

PNP-G7 Assay:

The alpha-amylase activity is determined by a method employing the PNP-G7 substrate. PNP-G7 is an abbreviation for 4,6-ethylidene($G_7$)-p-nitrophenyl($G_1$)-α,D-maltoheptaoside, a blocked oligosaccharide which can be cleaved by an endo-amylase, such as an alpha-amylase. Following the cleavage, the alpha-glucosidase included in the kit digest the hydrolysed substrate further to liberate a free PNP molecule which has a yellow color and thus can be measured by visible spectophometry at λ=405 nm (400-420 nm.). Kits containing PNP-G7 substrate and alpha-glucosidase is manufactured by Roche/Hitachi (cat. No. 11876473).

Reagents:

The G7-PNP substrate from this kit contains 22 mM 4,6-ethylidene-G7-PNP and 52.4 mM HEPES (2-[4-(2-hydroxyethyl)-1-piperazinyl]ethanesulfonic acid), pH 7.0.

The alpha-glucosidase reagent contains 52.4 mM HEPES, 87 mM NaCl, 12.6 mM $MgCl_2$, 0.075 mM $CaCl_2$, >4 kU/L alpha-glucosidase.

The substrate working solution is made by mixing 1 ml of the alpha-glucosidase reagent with 0.2 ml of the G7-PNP substrate. This substrate working solution is made immediately before use.

Dilution buffer: 50 mM EPPS, 0.01% (w/v) Triton X100 (polyethylene glycol p-(1,1,3,3-tetramethylbutyl)-phenyl ether ($C_{14}H_{22}(C_2H_4O)_n$(n=9-10))), 1mM $CaCl_2$, pH 7.0.

Procedure:

The amylase sample to be analyzed is diluted in dilution buffer to ensure the pH in the diluted sample is 7. The assay is performed by transferring 20 µl diluted enzyme samples to 96 well microtiter plate and adding 80 µl substrate working solution. The solution is mixed and pre-incubated 1 minute at room temperature and absorption is measured every 20 sec. over 5 minutes at OD 405 nm.

The slope (absorbance per minute) of the time dependent absorption-curve is directly proportional to the specific activity (activity per mg enzyme) of the alpha-amylase in question under the given set of conditions. The amylase sample should be diluted to a level where the slope is below 0.4 absorbance units per minute.

Phadebas Activity Assay:

The alpha-amylase activity can also be determined by a method using the Phadebas substrate (from for example Magle Life Sciences, Lund, Sweden). A Phadebas tablet includes interlinked starch polymers that are in the form of globular microspheres that are insoluble in water. A blue dye is covantly bound to these microspheres. The interlinked starch polymers in the microsphere are degraded at a speed that is proportional to the alpha-amylase activity. When the alpha-amylase degrades the starch polymers, the released blue dye is water soluble and concentration of dye can be determined by measuring absorbance at 620 nm. The concentration of blue is proportional to the alpha-amylase activity in the sample.

The amylase sample to be analysed is diluted in dilution buffer with the desired pH. One substrate tablet is suspended in 5 mL activity buffer and mixed on magnetic stirrer. During mixing of substrate transfer 150 µl to microtiter plate (MTP) or PCR-MTP. Add 30 µl diluted amylase sample to 150 µl substrate and mix. Incubate for 15 minutes at 37° C. The reaction is stopped by adding 30 µl 1M NaOH and mix. Centrifuge MTP for 5 minutes at 4000×g. Transfer 100 µl to new MTP and measure absorbance at 620 nm.

The amylase sample should be diluted so that the absorbance at 620 nm is between 0 and 2.2.

EnzChek® Assay:

For the determination of residual amylase activity an EnzChek® Ultra Amylase Assay Kit (E33651, Invitrogen, La Jolla, Calif., USA) was used.

The substrate is a corn starch derivative, DQ™ starch, which is corn starch labeled with BODIPY® FL dye to such a degree that fluorescence is quenched. One vial containing approx. 1 mg lyophilized substrate is dissolved in 100 microliters of 50 mM sodium acetate (pH 4.0). The vial is vortexed for 20 seconds and left at room temperature, in the dark, with occasional mixing until dissolved. Then 900 microliters of 100 mM acetate, 0.01% (w/v) TRITON® X100, 0.125 mM $CaCl_2$, pH 5.5 is added, vortexed thoroughly and stored at room temperature, in the dark until ready to use. The stock substrate working solution is prepared by diluting 10-fold in residual activity buffer (100 mM acetate, 0.01% (w/v) TRITON® X100, 0.125 mM $CaCl_2$, pH 5.5). Immediately after incubation the enzyme is diluted to a concentration of 10-20 ng enzyme protein/ml in 100 mM acetate, 0.01% (W/v) TRITON® X100, 0.125 mM $CaCl_2$, pH 5.5.

For the assay, 25 microliters of the substrate working solution is mixed for 10 second with 25 microliters of the diluted enzyme in a black 384 well microtiter plate. The fluorescence intensity is measured (excitation: 485 nm, emission: 555 nm) once every minute for 15 minutes in each well at 25° C. and the $V_{max}$ is calculated as the slope of the plot of fluorescence intensity against time. The plot should be linear and the residual activity assay has been adjusted so that the diluted reference enzyme solution is within the linear range of the activity assay.

Alpha-Amylase Activity (KNU(T))

The amylolytic activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU(T)) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

Glucoamylase Activity Assay (AGU)

Glucoamylase activity may be measured in Glucoamylase Units (AGU).

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
| --- | --- |
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
| --- | --- |
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

Determination of Pullulanase Activity (NPUN)

Endo-pullulanase activity in NPUN is measured relative to a Novozymes pullulanase standard. One pullulanase unit (NPUN) is defined as the amount of enzyme that releases 1 micro mol glucose per minute under the standard conditions (0.7% red pullulan (Megazyme), pH 5, 40° C., 20 minutes). The activity is measured in NPUN/ml using red pullulan.

1 ml diluted sample or standard is incubated at 40° C. for 2 minutes. 0.5 ml 2% red pullulan, 0.5 M KCl, 50 mM citric acid, pH 5 are added and mixed. The tubes are incubated at 40° C. for 20 minutes and stopped by adding 2.5 ml 80% ethanol. The tubes are left standing at room temperature for 10-60 minutes followed by centrifugation 10 minutes at 4000 rpm. OD of the supernatants is then measured at 510 nm and the activity calculated using a standard curve.

Determination of Lysophospholipase Activity (LLU)

Lysophospholipase activity in LLU is measured relative to Novozymes lysophospholipase standard. Lysophospholipase (EC 3.1.1.5) catalyzes the hydrolysis of L-alpha-lysophosphatidylcholine into glycerophosphocholine and free fatty acids. The activity of the enzyme is proportional to the amount of released free fatty acids. These are quantified using an enzymatic, colorimetric Wako NEFA-HR(2) kit at 37° C., pH 6.9. Samples are dissolved and diluted to approx. 0.00714 LLU/ml in a measuring flask with diluent (4.9 mM MgCl2, 5.0 mM CaCl2, 0.15% Brij, 10 mM sodium acetate, pH 5.5) and stirred for 15 minutes. The samples are further diluted with diluent (4.9 mM MgCl2, 5.0 mM CaCl2, 0.15% Brij, 10 mM sodium acetate, pH 5.5) to a final dilution of approx. 0.00714 LLU/ml. Absorbance is measured at 540 nm and the activity calculated using a standard curve.

Determination of Sugar Profile and Solubilised Dry Solids

DE can be calculated according to methods known in the art, as described in e.g., Rong et al., J. Food Science, vol. 74., nr. 1, C33-C40 (2009).

The sugar composition of the starch hydrolysates is determined by HPLC and glucose yield is subsequently calculated as DX. ° BRIX, solubilized (soluble) dry solids of the starch hydrolysates are determined by refractive index measurement.

Materials

Alpha-Amylase Variants

The alpha-amylase variants tested are variants of LE399 (SEQ ID NO: 14, previously disclosed in, e.g., WO 2002/010355), as described WO 2013/057143. LE399 comprises amino acids 1-37 of the alpha-amylase from *Bacillus amyloliquefaciens* (SEQ ID NO: 6) and amino acids 40-483 of the alpha-amylase from *Bacillus licheniformis* (SEQ ID NO: 1) with the following substitutions G48A T49I G107A H156Y A181T N190F I201F A209V Q264S. The substitutions in each variant as listed below are substitutions as compared to LE399. The position numbering is according to SEQ ID NO: 1.

LE399 is two amino acids shorter than SEQ ID NO: 1 in the N-terminal, i.e. there are no amino acids corresponding to positions 1 and 2 of SEQ ID NO: 1 in LE399. The alteration denoted in the tables as *2aH means insertion of H before the N-terminal V of LE399. A similar alteration in SEQ ID NO: 1 would be substitution of amino acid N2 with H, i.e. N2H (alternatively, deletion of amino acid A1 combined with substitution of amino acid N2 with H, i.e. A1*N2H). Likewise, the alterations denoted in the tables as *2aH *2bW means insertion of HW before the N-terminal V of LE399. A similar alteration in SEQ ID NO: 1 would be the substitutions A1H N2W.

Alpha-Amylase Variant A:
H68W+K176L+E185P+I201Y+H205Y+K213T+Q360S+ D416V+R437W

Alpha-Amylase Variant B:
H142W+K176L+E185P+I201Y+H205Y+K213T+Q360S+ D416V+R437W

Alpha-Amylase Variant C:
N2H+H133Y+K176L+E185P+Q360S+R437W

Alpha-Amylase Variant D:
K176L+E185P+I201Y+H205Y+K213T+Q360S+D416V+ R437W

Saccharification Enzyme

Saccharification Enzyme A: Dextrozyme DX 2.0× available from Novozymes A/S, having glucoamylase and pullulanase activity.

Saccharification Enzyme B: Optimax 4060 VHP available from DuPont/Genencor, having glucoamylase and pullulanase activity.

Saccharification Enzyme C: Dextrozyme DX 1.5× available from Novozymes A/S, having glucoamylase and pullulanase activity.

Saccharification Enzyme D: Dextrozyme DX Plus 1.5× available from Novozymes A/S, having glucoamylase and pullulanase activity.

| Enzyme | Activity |
| --- | --- |
| Saccharification Enzyme C | 279 AGU, 588.3 NPUN, 35.02 LLU |
| Saccharification Enzyme D | 378.2 AGU/g, 1574.0 NPUN/g, 35.37 LLU/g |
| Saccharification Enzyme B | 329 AGU/g, 666 NPUN_XD/g, 25.8 FAU (A)/g |
| Alpha-Amylase Variant A | 580 KNU (T)/g |

Exemplary Equipment
Gilson 215 liquid handler (Serial #: 259C9200)
50 mL Pyrex bottles (Item #: 1395-50) with septa
Small stir bars
Computer with Gilson 735 Sampler Software
Millipore 13 mm Millex Nylon 0.2 μm Syringe Filters (Item #: SLGNX13NK)
HPLC vials
Borosilicate test tubes, 16×100 mm (Item #: 14-961-29)

Example 1

100 kg of corn starch is slurried with tap water containing 100 ppm Ca2+ and the volume is adjusted to 225 liters. The pH is adjusted to 6.3 and 135 g Alpha-Amylase Variant is added.

This suspension is continuously pumped through a jet cooker (Hydro-Thermal Corp. Milwaukee) where it is heated to 105° C. injection and maintained at 105° C. for five minutes. The liquefied starch suspension is flash-cooled and pumped over into a saccharification tank where it is held for 1 hour at 95° C.

The pH of the liquefied starch is adjusted to 4.5 at 95° C. to stop the reaction and the batch is then spray-dried without purification. The DE of the spray-dried maltodextrin can be measured.

Substrates for saccharification are prepared by redissolving suitable amounts of this maltodextrin in deionized water and making up to approximately 30% DS. Aliquots of this substrate are then taken and heated to 50° C. and pH adjusted to 4.0. Different amounts of Saccharification Enzyme are added. The reaction mixtures may be sampled at set time intervals and the % dextrose in each sample determined by HPLC.

Example 2

Aliquots of the substrate prepared as in Example 1 are heated to 55° C. or 60° C. and the pH adjusted to 4.5 or 6.0. Saccharification Enzyme is added at varying amounts. The reaction mixtures are sampled and analysed as in Example 1.

Example 3

Aliquots of the substrate prepared as in Example 1 are incubated at 50° C., 55° C. and 60° C. at pH 3.5 and 4.0. Different amounts of Saccharification Enzyme are added. The reaction mixtures are sampled at set time intervals and analysed as in Example 1.

Example 4

Aliquots of the substrate prepared as in Example 1 are incubated at different pH values at 50° C. Saccharification Enzyme is added. The reaction mixtures are sampled at set time intervals and analysed as in Example 1.

Example 5

Substrates with different dry solids contents are prepared by dissolving 100 g of the maltodextrin from Example 1 in different amounts of deionized water. Samples are heated to 60° C. and adjusted to pH 4.5, or to 50° C. and pH 4.0, and Saccharification Enzyme is added. The reaction mixtures are sampled and analysed as in Example 1.

Example 6

A further batch of maltodextrin substrate is prepared as in Example 1. After 1 hour at 90° C. the pH is adjusted to 4.5 and the batch is spray-dried. The DE of maltodextrin can be measured.

Substrates for saccharification can be prepared by redissolving suitable amounts of maltodextrin in deionized water and adjusting the solids content to approximately 30% DS.

Aliquots of reconsistuted maltodextrin are heated to 50° C. and 55° C. and the pH adjusted to 4.0. Saccharification Enzyme is added. The reaction mixtures are sampled at regular intervals and the dextrose content determined by HPLC.

Example 7

Substrates with different dry solids contents are prepared by dissolving 100 g of the maltodextrin from Example 6 in different amounts of deionized water. Samples are heated to 55° C. and 60° C. and adjusted to pH 4.5, or to 55° C. and pH 4.0, and Saccharification Enzyme is added. The reaction mixtures ae sampled and analysed as in Example 1.

Example 8

A glucose syrup is prepared by treating a starch slurry containing 30% DS (30% Dry Solid) waxy maize starch, 40 ppm Ca2+ (as CaCl2) at pH 6.0 with 0.1 mg enzyme protein/g DS of Alpha-Amylase Variant. The temperature is kept at 95° C. for one hour and 80° C. for 72 hours.

Example 9A

Day 1: 125.2 kg of maize starch (C*PharmGel 03406, Cargill Europe Limited) having 56 ppm calcium is combined with 210 kg ion exchanged water and adjusted to conductivity of 501 μS/cm and pH 5.19. Liquozyme Supra (Novozymes NS) at enzyme dosage 0.25 kg/t DS is added. The suspension is pumped through a jet cooker where it is heated to 105° C. at flow 230 L/h for a hold time of 5 minutes. The jet cooked slurry is collected in a tank and temperature continuously adjusted to 95° C. and held for about 60 minutes, after which 260 kg slurry is collected. Dextrose equivalent is followed by DE measurement (osmometer). 55 minutes after the reaction tank is filled with the 260 kg slurry, the hydrolysis is stopped by adjusting pH to 2.8 with HCl. After approximately 30 minutes the pH is readjusted to 4.5 and temperature is decreased to 72° C. for storage of the slurry to the next day.

Day 2: Temperature measured at 72° C. and pH is adjusted to 4.5. Stirring in the reaction tank is stopped and the product is filtered to provide 774 L of filtrate 31.8° brix.

Day 3: Filtrate is spray-dried (temp in 200° C., temp out 82° C.) to provide 58.8 kg final product. Analysis of spray dried product shows DE of 10.7. Product is referred to as "Liquozyme Supra Maltodextrin"

Example 9B 123.7 kg of maize starch (C*PharmGel 03406, Cargill Europe Limited, ~88% DS) is combined with 209 kg demineralised water to provide a 33% DS starch slurry. pH is adjusted to 4.5, and conductivity is adjusted to 500 μS/cm with NaCl. Alpha-Amylase Variant A is added to approximately 75 KNU(T)/kg DS. The suspension is pumped through a jet cooker at 106° C.±1° C., followed by secondary jet cooking at 95° C. for about 60 minutes. After about an additional hour, the pH is adjusted to 2.4 to stop hydrolysis. After approximately 45 minutes, the pH is readjusted to 4.4 and temperature decreased to 72° C.

Temperature measured at 72° C. and pH is adjusted to 4.5. Stirring in the reaction tank is stopped and the product is filtered to provide 126 L of filtrate 32.6° brix. The filtrate is then spray dried temp in 200° C., temp out 80° C.) to provide 48 kg spray-dried powder, which shows DE of 11.6. This is referred to as "Alpha-Amylase Variant A Maltodextrin."

Liquozyme Supra Maltodextrin and Alpha-Amylase Variant A Maltodextrin are determined to have similar number-average molecular weight (Mn) and weight-average molecular weight (Mw), and thus, similar polydispersity (PD=Mw/Mn) values, as well as similar DP1 to DP10 distribution (data not shown).

Example 10

Substrates for saccharification are prepared by dissolving suitable amounts of maltodextrin prepared as in Example 9A-9B in deionized water and making up to approximately 33% DS. This solution pH is adjusted to 4.5. Aliquots of this substrate are taken and put into 50 mL Pyrex bottles. Different amounts of saccharification enzyme are then added. Samples are then heated to 60° C. in Gilson 215 saccharification robot. Samples are scheduled to be taken at set time intervals. The % dextrose, DP2, DP3, and DP4+ in each sample is determined by HPLC.

Saccharification conditions are as follows:

| | |
|---|---|
| Initial pH | 4.5 |
| Temperature | 60° C. |
| Maltodextrin DS | 33% |
| Sample weight (g) | 45 |

Example 11

Saccharification enzyme is Saccharification Enzyme C at 0.045% w/w dose level. Saccharification time is for 48 hours. The reaction mixtures are sampled and analysed as in Example 10.

Table 1 summarizes the saccharification results:

| Maltodextrin | DP1% | DP2% | DP3% | DP4+% |
|---|---|---|---|---|
| Alpha-Amylase Variant A Maltodextrin | 95.9 | 2.2 | 0.7 | 1.2 |
| Liquozyme Supra Maltodextrin | 95.4 | 2.2 | 0.7 | 1.7 |

Example 12

Saccharification enzyme is Saccharification Enzyme B at 0.038% w/w dose level. This is the exact same AGU dose level as in Example 11. Saccharification time is for 48 hours. The reaction mixtures are sampled at set time intervals and analysed as in Example 10.

Table 2 summarizes the saccharification results:

| Maltodextrin | DP1% | DP2% | DP3% | DP4+% |
|---|---|---|---|---|
| Alpha-Amylase Variant A Maltodextrin | 94.9 | 2.2 | 0.6 | 2.3 |
| Liquozyme Supra Maltodextrin | 93.9 | 2.1 | 0.6 | 3.3 |

Example 13

Saccharification enzyme is Saccharification Enzyme C at 0.045% w/w dose level. Active LE2488 is added to saccharification. Saccharification time is for 48 hours. The reaction mixtures are sampled and analysed as in Example 10.

Table 3 summarizes the saccharification results:

| Maltodextrin | DP1% | DP2% | DP3% | DP4+% |
|---|---|---|---|---|
| Alpha-Amylase Variant A Maltodextrin | 96.0 | 2.2 | 0.9 | 0.9 |
| Liquozyme Supra Maltodextrin | — | — | — | — |

Example 14

Saccharification enzyme is Saccharification Enzyme B at 0.038% w/w dose level. In addition, Alpha-Amylase Variant A is added to saccharification. Saccharification time is for 48 hours. The reaction mixtures are sampled and analysed as in Example 10.

Table 4 summarizes the saccharification results:

| Maltodextrin | DP1% | DP2% | DP3% | DP4+% |
|---|---|---|---|---|
| Alpha-Amylase Variant A Maltodextrin | 95.9 | 2.0 | 0.8 | 1.3 |
| Liquozyme Supra Maltodextrin | 94.4 | 2.0 | 0.7 | 2.9 |

Example 15

Saccharification enzyme is Saccharification Enzyme D at 0.033% w/w dose level. This is the exact same AGU dose level as in Example 11. Saccharification time is for 48 hours. The reaction mixtures are sampled and analysed as in Example 10.

Table 5 summarizes the saccharification results:

| Maltodextrin | DP1% | DP2% | DP3% | DP4+% |
|---|---|---|---|---|
| Alpha-Amylase Variant A Maltodextrin | 95.8 | 2.1 | 0.8 | 1.4 |
| Liquozyme Supra Maltodextrin | 95.7 | 2.2 | 0.8 | 1.4 |

The invention claimed is:

1. A process for producing a syrup comprising:
   a) liquefying an aqueous granular starch slurry with an alpha-amylase variant comprising a substitution at a position corresponding to one or more of positions 176, 185, 360 and/or 437 of SEQ ID NO: 1 to provide liquefied starch-containing material;
   b) saccharifying the liquefied starch-containing material in the presence of a glucoamylase, and a pullulanase derived from Bacillus deramificans, Bacillus subtilis, Bacillus amyloderamificans, or Bacillus acidopullulyticus and an alpha-amylase variant comprising an alteration at one or more positions corresponding to any of positions 1, 2, 68, 71, 126, 133, 142, 144, 156, 158, 176, 185, 201, 205, 213, 239, 279, 316, 318, 360, 416, 437 and 450 of SEQ ID NO: 1 to provide a dextrose syrup, and optionally
   c) isomerizing to provide a fructose syrup.

2. The process of claim 1, wherein the alpha-amylase variant is added in an amount of about 0.0001-3 mg enzyme protein per gram dry solids.

3. The process of claim 1, wherein the alpha-amylase variant comprises a substitution at position 176 and/or 185 of SEQ ID NO: 1.

4. The process of claim 1, wherein the pullulanase is derived from Bacillus deramificans.

5. The process of claim 1, wherein the starch slurry has 20-55% dry solids granular starch.

6. The process of claim 1, wherein at least 85% of the dry solids of the granular starch is converted into a syrup, e.g., a dextrose syrup or a fructose syrup.

7. The process of claim 1, wherein the granular starch is obtained from tubers, roots, stems, or whole grain.

8. The process of claim 1, wherein the granular starch is obtained from cereals.

9. The process of claim 1, wherein the granular starch is obtained from corn, cobs, wheat, barley, rye, milo, sago, cassava, tapioca, sorghum, rice or potatoes.

10. The process of claim 1, wherein the granular starch is obtained from dry milling of whole grain or from wet milling of whole grain.

11. The process of claim 1, wherein addition of the alpha-amylase variant in step a), step b), or a combination thereof results in higher DP1 product compared to a similar reaction without the alpha-amylase variant.

12. The process of claim 1, wherein addition of the alpha-amylase variant in step a), step b), or a combination thereof results in reduced DP4+product compared to a similar reaction without the alpha-amylase variant.

13. The process of claim 1, wherein addition of the alpha-amylase variant in step a), step b), or a combination thereof results in reduced DP2 product compared to a similar reaction without the alpha-amylase variant.

* * * * *